US011059000B2

(12) United States Patent
Koboshi et al.

(10) Patent No.: US 11,059,000 B2
(45) Date of Patent: Jul. 13, 2021

(54) METHOD FOR PRODUCING CARBON DIOXIDE GAS/MICRO-BUBBLES MIXED WATER AND PRODUCTION DEVICE THEREOF

(71) Applicant: Hot Album Tansansen Tablet, Inc., Hachiouji-shi (JP)

(72) Inventors: Shigeharu Koboshi, Hachiouji (JP); Hiroshi Yoshimoto, Hachiouji (JP)

(73) Assignee: Hot Album Tansansen Tablet, Inc., Tokyo (JP)

( * ) Notice: Subject to any disclaimer, the term of this patent is extended or adjusted under 35 U.S.C. 154(b) by 309 days.

(21) Appl. No.: 16/090,639

(22) PCT Filed: Apr. 6, 2017

(86) PCT No.: PCT/JP2017/014317
§ 371 (c)(1),
(2) Date: May 3, 2019

(87) PCT Pub. No.: WO2017/175817
PCT Pub. Date: Oct. 12, 2017

(65) Prior Publication Data
US 2019/0291061 A1  Sep. 26, 2019

(30) Foreign Application Priority Data
Apr. 7, 2016 (JP) .............................. JP2016-077204

(51) Int. Cl.
*B01F 3/04* (2006.01)
*A23L 2/00* (2006.01)
(Continued)

(52) U.S. Cl.
CPC ............ *B01F 3/04099* (2013.01); *A23L 2/00* (2013.01); *A61K 8/0204* (2013.01); *A61K 8/046* (2013.01);
(Continued)

(58) Field of Classification Search
CPC ................................ B01F 3/04099; A23L 2/00
See application file for complete search history.

(56) References Cited

U.S. PATENT DOCUMENTS

| 2014/0315719 A1* | 10/2014 | Rau ......................... A61K 8/39 |
| | | 504/358 |
| 2015/0150813 A1* | 6/2015 | Koboshi .................. A61K 8/86 |
| | | 424/700 |

FOREIGN PATENT DOCUMENTS

| JP | 2-255610 A | 10/1990 |
| JP | 10-276926 A | 10/1998 |

(Continued)

OTHER PUBLICATIONS

International Search Report for PCT/JP2017/014317 completed May 17, 2017 (2 pages).

*Primary Examiner* — Robert A Hopkins
(74) *Attorney, Agent, or Firm* — Brian B. Shaw, Esq.; Hater Secrest & Emery LLP

(57) ABSTRACT

[Problem]
A preparation of forming bubbles of carbon dioxide gas which is put into a micro-bubble generator is realized, unlike a conventional tablet, as a tablet which can retain an ability to neutralize and remove completely chlorine contained in tap water from start of dissolution of the tablet inside the micro-bubble generator to the completion of dissolution thereof, thereby providing a method for producing micro-bubbles of carbon dioxide gas by using the tablet and a device thereof.
[Solution]
There is provided a method for producing carbon dioxide gas/micro-bubbles mixed water in which a carbonated bathing agent is a tablet which is 7 mm or more both in tablet diameter and tablet thickness, 15 kg or more in tablet hardness, 10 wt % or less in tablet friability and from 5.5 to (Continued)

9.0 in pH immediately after dissolution of the tablet in hot water and the carbonated bathing agent contains at least one of the following body rendering agents and contains at least one of the following chlorine neutralizing compounds.

18 Claims, 4 Drawing Sheets

(51) Int. Cl.
| | |
|---|---|
| A61K 8/02 | (2006.01) |
| A61K 8/23 | (2006.01) |
| A61K 8/37 | (2006.01) |
| A61K 8/46 | (2006.01) |
| A61K 8/49 | (2006.01) |
| A61K 8/86 | (2006.01) |
| A61K 8/67 | (2006.01) |
| A61K 8/365 | (2006.01) |
| A61K 8/362 | (2006.01) |
| B01F 5/00 | (2006.01) |
| B01F 1/00 | (2006.01) |
| A61K 8/04 | (2006.01) |
| A61K 8/19 | (2006.01) |
| A61Q 19/10 | (2006.01) |

(52) U.S. Cl.
CPC .................. *A61K 8/19* (2013.01); *A61K 8/23* (2013.01); *A61K 8/362* (2013.01); *A61K 8/365* (2013.01); *A61K 8/37* (2013.01); *A61K 8/463* (2013.01); *A61K 8/466* (2013.01); *A61K 8/4973* (2013.01); *A61K 8/676* (2013.01); *A61K 8/86* (2013.01); *B01F 1/00* (2013.01); *B01F 3/04* (2013.01); *B01F 5/00* (2013.01); *A61K 2800/222* (2013.01); *A61Q 19/10* (2013.01); *B01F 2003/04858* (2013.01); *B01F 2003/04893* (2013.01); *B01F 2003/04943* (2013.01)

(56) References Cited

FOREIGN PATENT DOCUMENTS

| JP | 2000-119161 A | 4/2000 |
| JP | 2013-5861 A | 1/2013 |
| JP | 2014-4317 A | 1/2014 |

\* cited by examiner

METHOD FOR PRODUCING CARBON DIOXIDE GAS/MICRO-BUBBLES MIXED WATER AND PRODUCTION DEVICE THEREOF

TECHNICAL FIELD

The present invention relates to a method for producing carbon dioxide gas/micro-bubbles mixed water which remarkably improves blood flow promoting effects of a carbonated spring bathing agent and has excellent carbonated micro-bubble effects and relates to a device for easily producing the carbon dioxide gas/micro-bubbles mixed water.

BACKGROUND ART

A mixture which contains bicarbonate (sodium hydrogen carbonate or potassium hydrogen carbonate) and an organic acid is formed by compression molding, tablet-making or others to provide a bubble-forming composition (solid substance), and this process is applied to products such as a cleaning agent, a bathing agent, a bath water detergent, a pool-water disinfectant, etc. These products (solid substances) are advantageous in that they will rapidly dissolve when put into water while generating carbon dioxide gas by reaction of their components and are also effective in enhancing commercial value as they impart a comfortable feeling from use to consumers. In particular, in bath salts (also referred to as bathing agents), the effect on promoting blood circulation due to generation of carbon dioxide gas is widely used in a proactive manner.

On the other hand, very small bubbles, for example, those with a diameter of 0.05 mm or less, which are referred to as micro-bubbles, are considered to have a high cleaning ability in a shower unit, etc., and have been widely used. Micro-bubbles are also used because of their enhancing effect on promoting dissolution of oxygen into water and dissolution of a gas into water, where micro-bubbles are generated in closed water areas such as lakes, ponds and culture ponds.

Conventionally, as a micro-bubble shower which uses the micro-bubbles, there is known a tap-water pressure-based shower which uses a swirl flow (refer to Patent Document 1).

There is also known a combination which is obtained by using a technology which dissolves the carbon dioxide gas generating component in hot water with a technology which generates micro-bubbles to disinfect microorganisms in a liquid and purify the liquid (refer to for example, Patent Document 2).

The technology of Patent Document 1 is such that a carbon dioxide gas generating article like one found in various types of bathing agents is disposed as a gas generating article inside a gas-liquid mixer and an ejection port side of the gas-liquid mixer is connected to a shower head, and thus hot water obtained by mixing a bathing component with micro-bubbles is ejected from the shower head, by which cleaning effects and health promoting effects such as improvement of blood circulation can be expected to be obtained.

There is also available a shower head with water cleaning function in which a cartridge-type chlorine removing component is put into a grip portion of a shower head. And, it is also known that vitamin C is effective in removing chlorine (refer to Patent Document 3).

In the technologies described in Patent Documents 1 to 3, however, conventional bathing agent components and tablets are rapidly dissolved by being dissolved by a water flow due to a pressure of tap water, a carbon dioxide gas generating bathing agent continues to dissolve in a very short period of time, generated bubbles are very large in diameter and less likely to exhibit effects on skin and the inside of blood vessels even when contacting the body, in particular, where hot water at the time of taking a shower flows freely, hot water ejected from a shower head flows down rapidly after contacting the body and, thus, as compared with bathing in a bathtub, hot water is short in the period of time and also small in area when contacting the body. Therefore, the present inventor and others have found that in order to obtain the health promoting effects such as improvement of blood circulation described above, a bathing agent having an acid pH range or that having a short duration of dissolution is small in warm bath effects and completely ineffective and, therefore, have provided a number of patented technologies for solving problems (refer to Patent Document 4).

In subsequent experiments, the present inventor and others have, however, found that a carbon dioxide gas bathing agent or a bicarbonate ion bathing agent is severely suppressed for blood flow promotion and warming effects at the time of bathing by the presence of chlorine in tap water. A disinfectant such as chlorine in tap water is found to have such actions that it makes predominant all at once sympathetic nerves of autonomic nerves when absorbed through the skin and, as a result, cortisol is secreted from the adrenal cortex to contract the blood vessels, resulting in a decrease in blood flow. Thus, despite the development of carbonated bathing agents or systems of generating micro-bubbles of carbon dioxide gas that are high in warming effects at the time of bathing so that the body can be warmed only by taking a shower, the presence of chlorine is found to adversely influence these effects if it is present and substantially reduce the warming effects at the time of bathing.

Further, chlorine not only spoils the warming effects at the time of bathing but also damages protein of the skin and hair. Thus, when chlorine reacts with protein of the skin and hair, it ages not only the skin and hair by damaging them but also causes various types of skin troubles. It is also reported that chlorine reacts with sebum and easily produces carcinogenic trihalomethane and may cause cancer.

As to removal of residual chlorine in tap water, Patent Document 3 has described "a bathing agent, etc., which contain inorganic reducing substances such as sodium thiosulfate, sodium sulfite, potassium pyrosulfite; organic reducing substances such as ascorbic acid and sodium ascorbate; and various plant-based and herb-based reducing substances such as catechins, polyphenols, flavonoids, lycopene, anthocyanin, and xanthophylls." In this document, it is described that when the bating agent is put in tap water and dissolved, residual chlorine in tap water can be removed. However, the present inventor and others have found that, where the bathing agent described in the document is a tablet, after the tablet becomes wet by tap water and exposed to water, the above-described reducing compounds react with chlorine in tap water before the tablet is not yet dissolved completely, and if the tablet remains approximately half, it will be deprived of a chlorine neutralizing and removing ability. And, it has been found that, in the case of a bathing tablet used in a bathtub, there will be no serious problem if a user takes a bath after the elapse of a certain period of time from when the tablet has been put in the bathtub, however, this will pose a serious problem in a carbon dioxide gas micro-bubble generator or a production device which is used in a shower head through which water is poured on the body within one second from ejection of water, a chlorine removing ability must be retained until the tablet has been completely dissolved, loss of the chlorine removing ability while the tablet remains is a critical defect when the tablet is used as a bathing agent for shower and a preparation of generating micro-bubbles of carbon dioxide gas, and even any effective chlorine removing agent or any removing system available in conventional technologies would not provide such an effective method for exhibiting high blood flow promotion and warming effects at the time of bathing that have been attained by a micro-bubble generating system of the present invention.

A carbon dioxide gas bathing agent which forms bubbles in an acid range is hardly taken into blood vessels which are neutral in pH due to the fact that its main component is carbon dioxide gas, thereby providing no significant warming effects at the time of bathing. However, where a bicarbonate ion releasing bathing agent which is neutral in pH is used, bicarbonate is combined with an organic acid in a special granulation method, by which carbon dioxide gas is less likely to be generated in principle in a neutral pH range, so that the agent vigorously reacts to generate carbon dioxide gas even if its pH value is neutral, dissociating highly concentrated bicarbonate ions by a neutralization reaction and dissolving a large quantity of bicarbonate ions in hot water, thus making it possible to exhibit high warming effects at the time of bathing. However, the present inventor and others have experimentally shown that in this case as well, blood flow promoting effects are substantially suppressed, if chlorine ions remain in hot water in a large quantity.

According to the research carried out by the present inventor and others, hydrogen ions, etc., occurring from a combination of bicarbonate with citric acid or neutralization reactions are very slow in chlorine removing reactions and need a reaction time of several dozens of minutes or several hours. Where water is poured and in contact with the body immediately after generation of micro-bubbles of carbon dioxide gas as found in hot water at the time of taking a shower, it is necessary to add a reducing compound, for example, ascorbic acid such as vitamin C, ascorbate or sodium thiosulfate, which are conventionally known.

However, the present inventor and others have experimentally found a problem that in the case of a tablet which is composed of sodium bicarbonate and an organic acid such as citric acid, in particular, a conventional-type tablet which is not subjected to special granulation and low in hardness, due to permeation of water, even if any of these reducing substances having a chlorine neutralizing ability are added to a tablet, the substance undergoes oxidation/reduction reactions preferentially if water enters, and when the tablet is dissolved by approximately half, it is already deprived of the chlorine removing ability. That is, such a defect has been found that when water permeates in the tablet and penetrates thereinto, the permeated water flows around the tablet in its entirety, and when the tablet becomes wet, a permeation flow occurs so that water will flow all over the tablet, chlorine in hot water undergoes oxidation/reduction reactions selectively with the reducing substance, and when the tablet is dissolved by approximately half, chlorine removing effects disappear. It has also been found that warming effects by taking a shower receive a great influence, as compared with the warming effects by bathing in a bathtub in particular, and the tablet which is not yet dissolved but remains inside the carbon dioxide gas micro-bubble generator is deprived of the ability to neutralize and remove chlorine. And, this will severely hinder a blood flow increase as an object just by taking a shower and the tablet cannot be said to be a commercial product.

Tap water is supplied to households, with a water pressure applied. The water pressure is based on the same standard across the country but varied to some extent. A lower limit is 1.5 kgf/cm$^2$, an upper limit is 7.5 kgf/cm$^2$, and an ideal water pressure is to be from 2.0 to 4.0 kgf/cm$^2$. Meanwhile, the present inventor and others have also found a problem that unless an extremely large quantity of a reducing substance is added into a micro-bubble generator used under such a high water pressure, chlorine in permeated tap water will undergo oxidation/reduction reactions preferentially with a chlorine-neutralizing reducing agent in a conventional-type tablet which is low in hardness, and it will be decreased in chlorine removing ability, and under such a water pressure of water flow that tap water reaches the face and the skin within 0.3 seconds after ejection of the water, the tablet loses substantially the chlorine removing ability when it is not yet dissolved, and this is an unavoidable problem in actual daily showering because the water pressure described above is normal water pressure found anywhere.

Therefore, with regard to a bathing agent for shower as a carbon dioxide gas micro-bubble generator, from the moment when a tablet starts to dissolve to the completion of dissolution, that is, after a last piece of the tablet has been used up completely, it is necessary to retain the chlorine neutralizing ability and continuously retain the chlorine removing ability. It is, therefore, strongly desired to develop an improved technology for realizing the above.

PRIOR ART DOCUMENTS

Patent Documents

[Patent Document 1] Japanese Published Unexamined Patent Application No. 2008-229516
[Patent Document 2] Japanese Published Unexamined Patent Application No. 2011-194390
[Patent Document 3] Japanese Published Unexamined Patent Application No. 2000-119161
[Patent Document 4] Japanese Published Unexamined Patent Application No. 2014-4317

SUMMARY OF THE INVENTION

Problems to be Solved by the Invention

The present invention has been made for solving the above-described problems and a first object thereof is to realize that a preparation of forming bubbles of carbon dioxide gas which is accommodated in a micro-bubble generator is a tablet which retains an ability to neutralize and remove completely chlorine contained in tap water from the time when the tablet starts to dissolve inside the micro-bubble generator up to the time when the tablet has dissolved completely, as compared with a conventional tablet, and to provide a method for producing micro-bubbles of carbon dioxide gas by using the tablet and a device thereof.

A second object of the present invention is to provide a method for producing micro-bubbles of carbon dioxide gas and a device thereof in which where a tablet starts to dissolve and generation of carbon dioxide gas takes place, bubbles smaller in diameter are generated continuously and stably for a longer period of time, and also chlorine is completely removed from the time when the tablet starts to dissolve to the time when it has dissolved completely, in a state of chlorine-free hot water, bicarbonate ions at a maximum concentration due to a neutralization reaction of carbon dioxide gas in water are showered onto the body, and also due to complete removal of chlorine, predominance of the sympathetic nerves on percutaneous absorption by a disinfectant is avoided, dilation of blood vessels with predominance of the para-sympathetic nerves is caused to maximize an increase in blood flow, and warming effects at the time of bathing are exhibited to the maximum extent.

Means for Solving the Problems

In order to attain the above-described objects, the present invention is arranged as follows.
[Invention 1]
A method for producing micro-bubbles mixed water in which hot water guided into a water channel having a micro-bubble generating portion installed between an inlet port and an ejection port of hot water is mixed with micro-bubbles (very small bubbles) obtained by dissolving in hot water a carbonated bathing agent accommodated in the micro-bubble generating portion, and ejected from the ejection port to obtain micro-bubbles mixed water,
the method for producing carbon dioxide gas/micro-bubbles mixed water in which the carbonated bathing agent accommodated in the micro-bubble generating portion is a compression molded tablet formed by compression molding in the presence of bicarbonate, an organic acid and polyethylene glycol, and
the method for producing carbon dioxide gas/micro-bubbles mixed water in which the carbonated bathing agent is a tablet which is 7 mm or more both in tablet diameter and tablet thickness, 15 kg or more in tablet hardness, 10 wt % or less in tablet friability and from 5.5 to 9.0 in pH immediately after dissolution of the tablet in hot water, and the carbonated bathing agent contains at least one of the following body rendering agents and at least one of the following chlorine neutralizing compounds.
[Body Rendering Agents]
Alkane sulfonate with a carbon number of 6 to 18, olefin sulfonate with a carbon number of 6 to 18, sucrose fatty acid ester, sodium sulfate and magnesium sulfate
[Chlorine Neutralizing Compounds]
L-ascorbic acid, L-ascorbate, thiosulfate, sulfite, erythobic acid and erythobate
[Invention 2]
The method for producing carbon dioxide gas/micro-bubbles mixed water according to the above-described Invention 1 in which the body rendering agent is contained at a ratio of 1:10 to 1:1000 in relation to an organic acid.
[Invention 3]
The method for producing carbon dioxide gas/micro-bubbles mixed water according to the above-described Invention 1 or Invention 2 in which the chlorine neutralizing compound is contained at 8 wt % or less in relation to an organic acid.
[Invention 4]
The method for producing carbon dioxide gas/micro-bubbles mixed water according to any one of the above-described Invention 1 to Invention 3 in which the body rendering agents are alkane sulfonate with a carbon number of 6 to 8 and olefin sulfonate with a carbon number of 6 to 8.
[Invention 5]
A device of producing micro-bubbles mixed water in which a mixture of hot water guided into a water channel having a micro-bubble generating portion installed between an inlet port and an ejection port of hot water with micro-bubbles (very small bubbles) obtained by dissolving in hot water a carbonated bathing agent accommodated in the micro-bubble generating portion is ejected from the ejection port to obtain micro-bubbles mixed water,
the device of producing carbon dioxide gas/micro-bubbles mixed water in which the carbonated bathing agent accommodated in the micro-bubble generating portion is a compression molded tablet formed by compression molding in the presence of bicarbonate, an organic acid and polyethylene glycol, and
the device of producing carbon dioxide gas/micro-bubbles mixed water in which the carbonated bathing agent is a tablet which is 7 mm or more both in tablet diameter and tablet thickness, 15 kg or more in tablet hardness, 10 wt % or less in tablet friability and from 5.5 to 9.0 in pH immediately after dissolution of the tablet in hot water, and the carbonated bathing agent contains at least one of the body rendering agents and at least one of the following chlorine neutralizing compounds.
[Body Rendering Agents]
Alkane sulfonate with a carbon number of 6 to 18, olefin sulfonate with a carbon number of 6 to 18, sucrose fatty acid ester, sodium sulfate and magnesium sulfate
[Chlorine Neutralizing Compounds]
L-ascorbic acid, L-ascorbate, thiosulfate, sulfite, erythobic acid and erythobate
[Invention 6]
The device of producing carbon dioxide gas/micro-bubbles mixed water according to the above-described Invention 5 in which the body rendering agent is contained at a ratio of 1:10 to 1:1000 in relation to an organic acid.
[Invention 7]
The device of producing carbon dioxide gas/micro-bubbles mixed water according to the above-described Invention 5 or Invention 6 in which the chlorine neutralizing compound is contained at 8 wt % or less in relation to an organic acid.
[Invention 8]
The device of producing carbon dioxide gas/micro-bubbles mixed water according to any one of the above-described Invention 5 to Invention 7 in which the body rendering agents are alkane sulfonate with a carbon number of 6 to 18 and olefin sulfonate with a carbon number of 6 to 18.
[Invention 9]
The device of producing carbon dioxide gas/micro-bubbles mixed water according to any one of the above-described Invention 5 to Invention 8 which is provided with a shower head portion and a shower body which are arranged integrally or arranged in a combined manner and in which the carbon dioxide gas micro-bubble generating portion is disposed at any one of the following positions (1) to (6):
(1) Arrangement of being disposed at the shower head portion,
(2) Arrangement of being disposed inside the shower body,
(3) Arrangement of being disposed between the shower head portion and the shower body or a connection portion of the shower head portion with the shower body or across the connection portion,
(4) Arrangement of being disposed at a terminal end portion of a water supplying hose connected to the shower body,
(5) Arrangement of being disposed at a leading end portion of the water supplying hose connected to the shower body, and (6) Arrangement of being disposed at a middle portion of the water supplying hose connected to the shower body.
[Invention 10]
The device of producing carbon dioxide gas/micro-bubbles mixed water according to any one of the above-described Invention 5 to Invention 9 in which the carbon dioxide gas micro-bubble generating portion can be attached in a detachable manner by simple one-touch operation.
[Invention 11]
The device of producing carbon dioxide gas/micro-bubbles mixed water according to any one of the above-described Invention 5 to Invention 10 in which the carbon dioxide gas micro-bubble generating portion is made with a transparent material, so that a state of dissolution of the carbonated bathing tablet accommodated in the carbon dioxide gas micro-bubble generating portion and the presence or absence of the tablet can be visually observed from outside.
[Invention 12]
The device of producing carbon dioxide gas/micro-bubbles mixed water according to any one of the above-described Invention 5 to Invention 11 in which at least a part of the device of producing carbon dioxide gas/micro-bubbles mixed water and at least a part of a member which constitutes a water channel thereinside are made with a transparent material, and hot water which flows inside the water channel can be observed visually from outside.

Hereinafter, a detailed description will be given of the present invention.
In the present invention, the carbon dioxide gas micro-bubble generator may be also described as a shower head that is used in combination with a carbonated tablet. Further, the bathing agent is used by being loaded or inserted in the shower head, which means that the tablet is loaded into the carbon dioxide gas micro-bubble production device and which includes a case that the bathing agent is loaded in a flow channel of tap water or hot tap water leading to the shower head.

Effects of the Invention

Unlike a conventional tablet, the tablet of the present invention is granulated by a special granulation method, formed by compression molding so as to be high in hardness, excellent in bubble-forming property to form fine bubbles of carbon dioxide gas intensively for a prolonged period of time, despite its neutrality, and dissolved in hot water while generating highly concentrated bicarbonate ions. Then, the tablet completely neutralizes and removes residual chlorine from the start of dissolution of the tablet to the point of the dissolution. Therefore, the effects of increasing blood flow are maximized and warming effects at the time of bathing are also exhibited to the maximum extent. Further, even where the carbonated micro-bubble generator into which the tablet is loaded is set in a shower head or set at a part of a hose between a faucet and the shower head, the tablet is able to effectively remove chlorine until complete dissolution thereof, thereby attaining the above-described first and the second objects of the present invention.

While it is known that L-ascorbate represented by L-ascorbic acid and sodium L-ascorbate; thiosulfate represented by sodium thiosulfate; sulfite represented by sodium sulfite; erythobic acid; and erythobate are able to neutralize chlorine in tap water, the present inventor and others have found that where these chlorine neutralizing compounds are added to a tablet having a conventional composition and the tablet is set in a shower head, the tablet exhibits its ability to neutralize chlorine immediately after starting to take a shower, however, when the tablet is dissolved by about ⅓ to ½, it is rapidly decreased in chlorine neutralizing ability and when the tablet is dissolved by 50% or more, it is deprived of the chlorine neutralize ability and fails to exhibit chlorine removing effects, which is somewhat related with a certain or higher water pressure.

Further, the tablet of the present invention is able to form bubbles of carbon dioxide gas stably and continuously despite its neutrality and also able to make bubbles of carbon dioxide gas into fine microsize bubbles with a diameter smaller than a certain level. The tablet is able to enlarge a total surface area value of bubbles, drastically increase dissociation and production of bicarbonate ions resulting from a neutralization reaction of carbon dioxide gas with water or hot water and form microsize bubbles slowly for a prolonged period of time, by which carbon dioxide gas components are turned into bicarbonate ions and dissolved sufficiently into water or hot water. After dissolution, since the water or hot water is neutral in pH, highly concentrated bicarbonate spring is prepared and bicarbonate ions are absorbed through the skin to the maximum extent to drastically increase bicarbonate ions in blood, exhibiting health effects such as promotion of blood circulation and elevation of body temperature to the maximum extent. Thus, the above-described second object of the present invention is attained.

As described above, in the present invention, the tablet is prepared so as to have a specific composition, or in addition to this specific composition due to a tablet hardness specification and a tablet friability specification, the tablet is dissolved slowly for a prolonged period of time and chlorine can be efficiently neutralized and removed over the long-time dissolution of the tablet, by which the second object of the present invention can be favorably attained. In addition to the above, the present invention also exhibits the following working effects.

Mineral ions of calcium, magnesium, copper, etc., which are attached to surfaces of protein, keratin, etc., of the scalp and hair to effect ionic bonding adhere and accumulated in hair roots at high concentrations, thereby causing hair root mineral dirt. The hair root mineral dirt, which is cation, forms ionic bonding with minus ions of the skin and keratin. Therefore, ionic bonding cannot be removed by a chemical detergent. As a result, the dirt is turned into perennial sebum and is the source for odors which develop in a few hours even after hair is rinsed repeatedly. Thus, a user finds it difficult to wash away the mineral sebum dirt cleanly by taking a shower using synthetic detergent-based soap or shampoo. However, according to the present invention, such cleaning effects have been confirmed from photographs of hair roots that free and small-molecule bicarbonate ions contain the mineral sebum dirt like an inclusion compound and remove the dirt by washing, thereby eliminating a source of odor. It has also been confirmed that not only in the case of bathing in a bathtub or footbath but also in the case of taking a shower, odor is substantially eliminated for several days after bathing despite the fact that a user just takes a shower. In addition to the second object of the present invention such as increased effects of warming the body and sound sleeping, there have also been confirmed effects of making skin and hair beautiful, along with odor removing effects and others.

Figure 1:
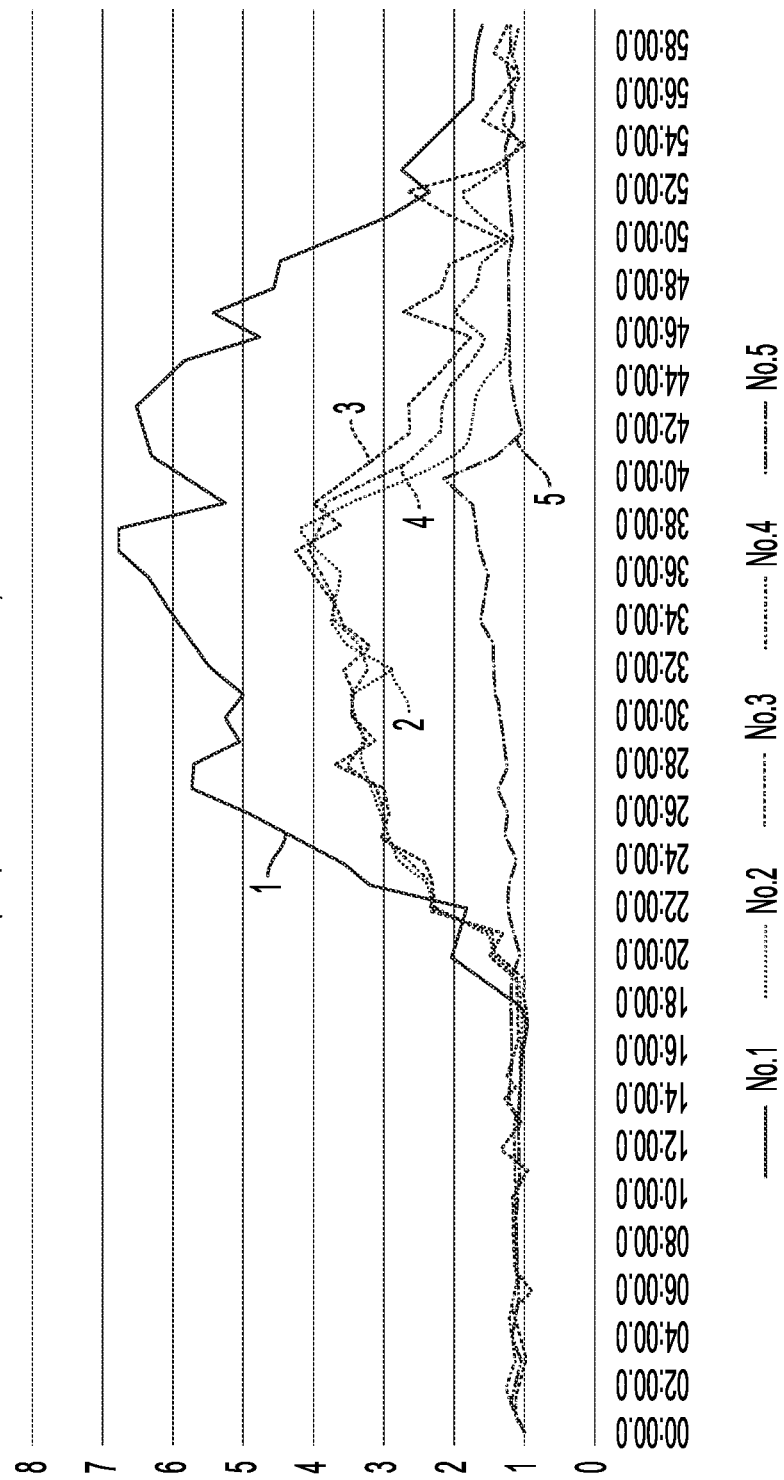
FIG. 1 is a graph which shows a tissue blood flow volume at the time of bathing when measured according to a blood flow measurement pattern in Reference Example-1.

Hereinafter, a description will be given of the method for producing micro-bubbles mixed water according to the present invention (hereinafter, simply referred to as a production method from time to time) and the device of producing micro-bubbles mixed water (hereinafter, simply referred to as a production device from time to time) by referring to drawings (FIG. 2 to FIG. 7).

The present invention relates to a production method for micro-bubbles mixed water that has not only carbonate spring bathing effects but also has micro-bubble effects and a production device which can easily obtain the micro-bubbles mixed water. This is a technology which is expected to obtain cleaning effects and also health promoting effects such as promotion of blood circulation by ejecting hot water mixed with micro-bubbles of carbon dioxide gas (ejection of shower) from an ejection port (shower ejection port) of the production device.

In the following example of the present invention, as a production device 1, there is shown such an arrangement that a micro-bubble generating portion 2 for accommodating a carbonated bathing agent (carbonate spring tablet) T is installed in a shower unit 10 arranged so as to be composed of a shower head portion 11 having a shower ejection port 13 and a shower body 12 acting as a handle when used. Hot water is supplied to the shower unit 10 via a hose 3 connected to the shower body 12.

Figure 2:
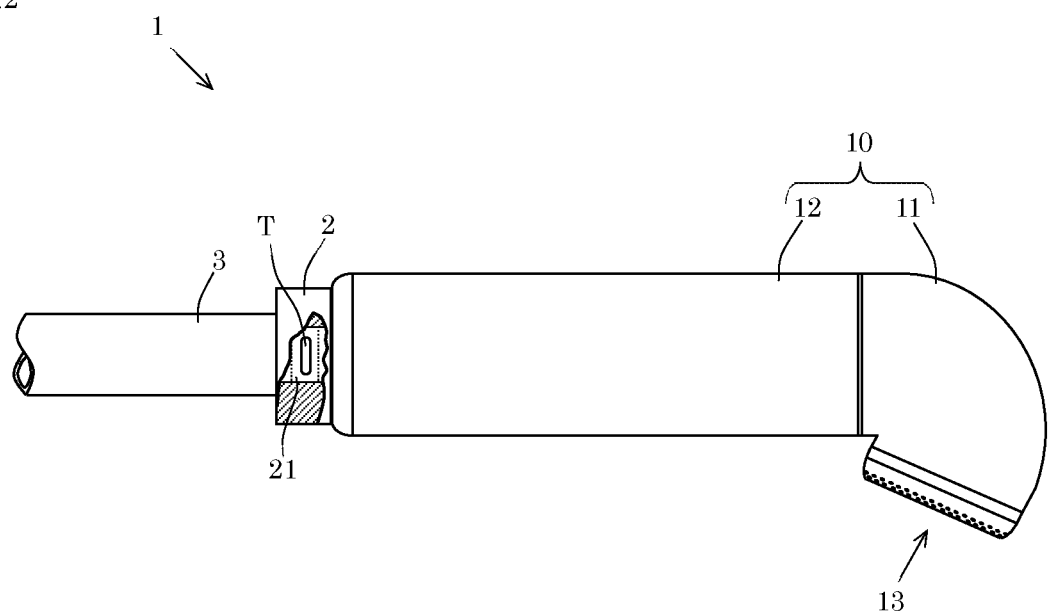
FIG. 2 is a schematic arrangement diagram which shows one example of a device of producing micro-bubbles mixed water according to the present invention (placed at a terminal end portion of a hose connected to a shower body).
Figure 3:
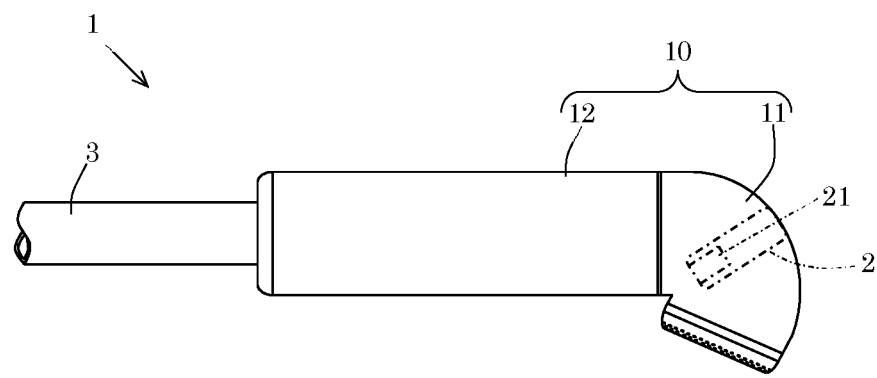
FIG. 3 is a schematic arrangement diagram which shows another example of a position at which a micro-bubble generating portion is disposed (placed at a shower head portion).
Figure 4:
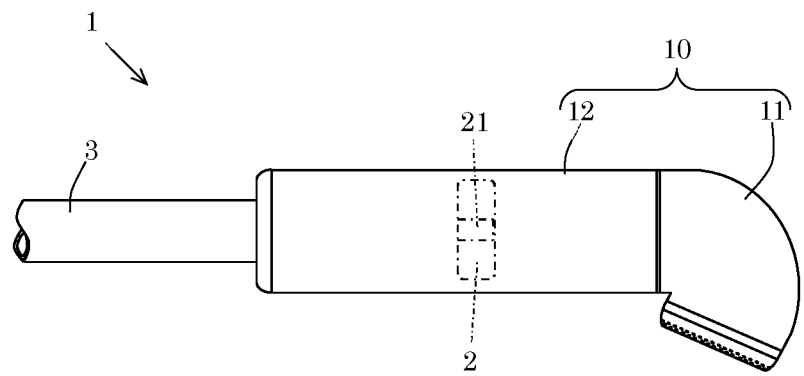
FIG. 4 is a schematic arrangement diagram which describes still another example of a position at which the micro-bubble generating portion is disposed (placed inside a shower body).
Figure 5:
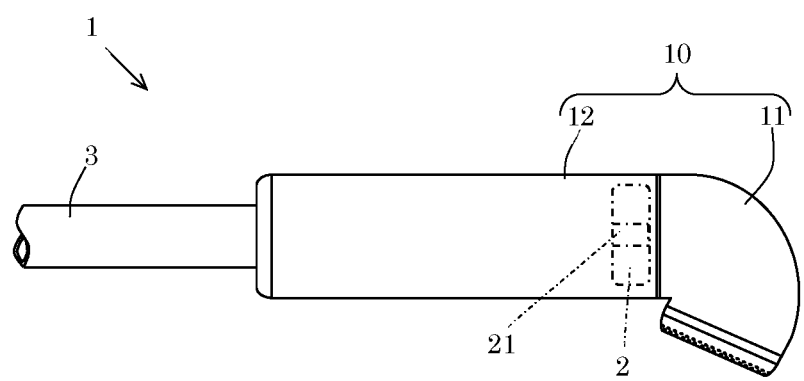
FIG. 5 is a schematic arrangement diagram which describes still another example of a position at which the micro-bubble generating portion is disposed (placed at a body side of a connection portion of the shower body with the shower head portion).
Figure 6:
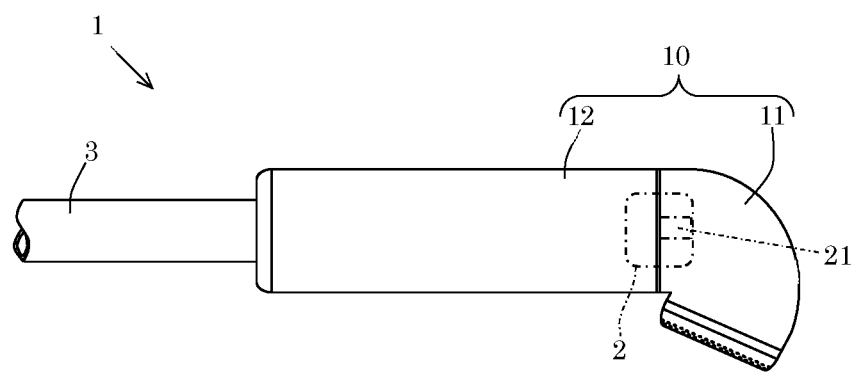
FIG. 6 is a schematic arrangement diagram which describes still another example of a position at which the micro-bubble generating portion is disposed (placed across the connection portion of the shower body with the shower head portion).
Figure 7:
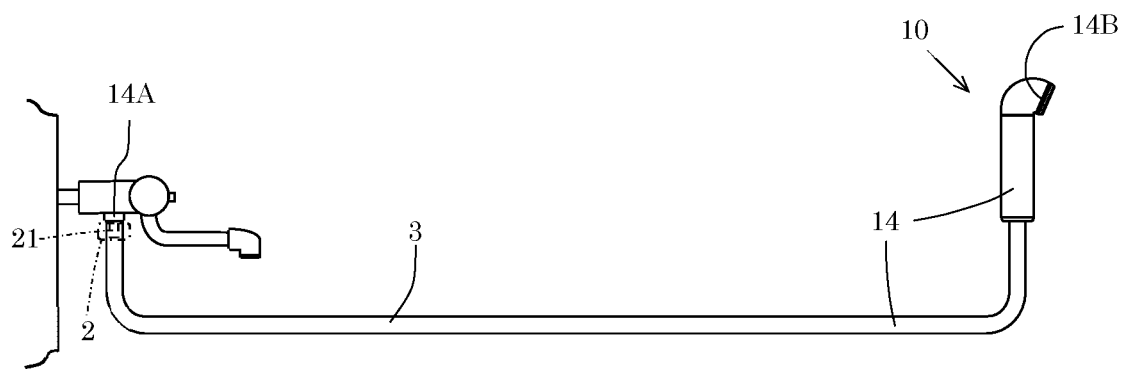
FIG. 7 is a schematic arrangement diagram which describes still another example of a position at which the micro-bubble generating portion is disposed (placed at a leading end portion of a hose connected to the shower body).

In FIG. 2, the shower head portion 11 and the shower body 12 may be formed integrally to give an integral arrangement or they may be formed separately and connected or joined together so as to be integral. Alternatively, the shower head portion 11 may be directly or indirectly connected so as to change a direction or an angle in relation to the shower body 12.

The micro-bubble generating portion 2 is installed at an inlet port 14A of hot water, an ejection port 14B thereof, or at any site of a water channel 14 between them, that is, at any site of a water supply channel from a leading end portion of the hose 3 connected to a water supply device such as a water heater, a tap water faucet, a water supply unit and a hot water faucet to a shower ejection port 13, which is a water supply channel of hot water. Accordingly, the carbonated bathing agent T accommodated at the micro-bubble generating portion 2 is dissolved by hot water which flows inside the water channel, and carbon dioxide gas generated by the dissolution is changed into micro-bubbles (very small bubbles) in hot water and mixed with the hot water to give micro-bubbles mixed water.

Next, a description will be given of an arrangement example of accommodating the carbonated bathing agent T in the micro-bubble generating portion 2.

The micro-bubble generating portion 2 is arranged to have a tablet accommodating portion 21 which is provided with a mesh-body like partition constitution through which hot water can pass upstream and downstream of a position of accommodating the carbonated bathing agent T. In this state of accommodation, the agent is disposed inside the water channel 14 of hot water and dissolved by being in contact with hot water flowing inside the water channel 14, thereby generating carbon dioxide gas to give micro-bubbles.

Figure 8:
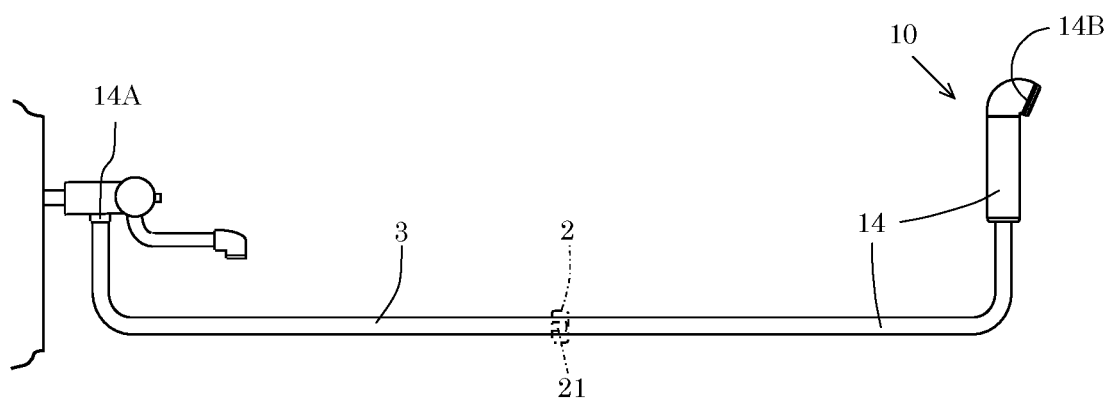
FIG. 8 is a schematic arrangement diagram which describes still another example of a position at which the micro-bubble generating portion is disposed (placed at a middle portion of the hose connected to the shower body).

The micro-bubble generating portion 2 is preferably disposed at any one of the positions (1) to (6) given below.
(1) Arrangement of being disposed at the shower head portion 11 (for example, an arrangement shown in FIG. 3)
(2) Arrangement of being disposed inside the shower body 12 (for example, an arrangement shown in FIG. 4)
(3) Arrangement of being disposed at a body side of a connection portion of the shower head portion 11 with the shower body 12 (for example, an arrangement shown in FIG. 5) or the connection portion of the shower head portion 11 with the shower body 12 (including an arrangement of being disposed across the connection portion, for example, an arrangement shown in FIG. 6)
(4) Arrangement of being disposed at a terminal end portion of the hose 3 connected to the shower body 12 (for example, an arrangement shown in FIG. 2)
(5) Arrangement of being disposed at a leading end portion of the hose 3 connected to the shower body 12 (for example, an arrangement shown in FIG. 7)
(6) Arrangement of being disposed at a middle portion of the hose 3 connected to the shower body 12 (for example, an arrangement shown in FIG. 8)

In the case of the above arrangement shown in (3), the micro-bubble generating portion 2 may be arranged so as to be built-in or incorporated in a terminal end portion of the hose 3, the terminal end portion of the hose 3 may be arranged so as to be connected to the micro-bubble generating portion 2, or the terminal end portion of the hose 3 may be arranged so as to be connected to the micro-bubble generating portion 2 connected or joined to the shower body 12 (an arrangement example shown in FIG. 2).

In the case of the above arrangement shown in (4), the micro-bubble generating portion 2 may be arranged so as to be built-in or incorporated in the leading end portion of the hose 3, the leading end portion of the hose 3 may be arranged so as to be connected to the micro-bubble generating portion 2, or the leading end portion of the hose 3 may be arranged so as to be connected to the micro-bubble generating portion 2 connected or joined to a faucet portion.

In the case of the above arrangement shown in (5), the micro-bubble generating portion 2 may be arranged so as to be built-in or incorporated in the middle portion of the hose 3. Or, two (a plurality of) hoses 3 are arranged and the micro-bubble generating portion 2 may be arranged so as to be built-in or incorporated in an interconnected portion of the two hoses 3 or the micro-bubble generating portion 2 may be arranged so as to function as a connection member of the two hoses 3.

The tablet accommodating portion 21 of the micro-bubble generating portion 2 is arranged so as to be attached to or detached from the shower head portion 11 or the shower body 12, by which the carbonated bathing agent T can be easily accommodated or added.

Further, the micro-bubble generating portion 2 is not limited to such an arrangement that, as shown in the above example, it is incorporated into the production device 1 as a part of an arrangement element of the production device 1 but may be such an arrangement that it is arranged separately from the shower head portion 11 and the shower body 12, connected to the shower head portion 11, the shower body 12 or the hose 3 and, thereby, disposed in a water channel of hot water.

In particular, the micro-bubble generating portion 2 is made so as to have an attachable/detachable arrangement, by which the carbonated bathing agent T can be accommodated or added easily and quickly. In the case of the attachable/detachable arrangement, the micro-bubble generating portion 2 in its entirety may be arranged so as to be attached in a detachable manner, or only the tablet accommodating portion 21 which is a portion of accommodating the carbonated bathing agent (carbonate spring tablet) T may be arranged so that it can be attached in a detachable manner.

It is also possible to form the micro-bubble generating portion 2 with a transparent material such as a transparent synthetic resin, thereby realizing such an arrangement that the carbonated bathing agent T accommodated into the micro-bubble generating portion 2 can be visually observed from outside the production device 1. According to the above-described arrangement, it is possible to easily understand the presence or absence of the carbonated bathing agent T accommodated in the micro-bubble generating portion 2 and an extent of dissolution from outside the production device 1.

Further, at least a part of the shower head portion 11 and/or the shower body 12 and at least a part of a member which constitutes a water channel thereinside are formed with a transparent material, thus making it possible to realize such an arrangement that hot water flowing in the water channel can be visually observed from outside the production device 1. According to the above arrangement, it is possible to easily understand from outside the production device 1 whether or not the carbonated bathing agent is dissolved in hot water or it is present, that is, whether micro-bubbles are generated or not.

As described above, for example, a skin cleaning agent prepared by making sodium ascorbate into a solid form is effective in removing chlorine contained in tap water but disadvantageous in that when the skin cleaning agent is used at the time of taking a shower, chlorine removing effects will disappear at the latter half of dissolution thereof.

Therefore, according to one aspect of the present invention, where the chlorine neutralizing compound is L-ascorbic acid, for example, L-ascorbate represented by sodium L-ascorbate or thiosulfate represented by sodium thiosulfate and also even where the tablet which is formed with sulfite, erythobic acid or erythobate is loaded into a shower head and used, for example, at the time of taking a shower other than bathing in a bathtub, the tablet exhibits an effective chlorine neutralizing ability to the maximum extent even at the latter half of the dissolution thereof. In general, a bathing agent specially used in a bathtub is able to substantially remove chlorine within a few hours only by the presence of an organic acid, etc. Further, chlorine which is a target can be removed only by addition of such a chlorine neutralizing compound as described in the present invention. However, the present invention is to provide an effect on a problem posed when used for generating micro-bubbles of carbon dioxide gas at the time of taking a shower and also to provide a newly exerted effect on a problem posed by a new product concept of a bathing agent for shower.

In addition to a requirement for the tablet with a specific composition which includes the above-described chlorine neutralizing compound, where the tablet is prepared by a granulation method of the present invention according to such a specification that is high in tablet hardness and low in tablet friability, and even when the tablet is used in particular for a shower by being loaded into the shower head which is a carbon dioxide gas micro-bubble generator, the tablet or even a last piece thereof exhibits effectively health promoting effects such as improvement of blood circulation and elevation of body temperature to the maximum extent even at the latter half of dissolution of the tablet.

Hereinafter, a detailed description will be given of the carbonated bathing agent used in the present invention. At first, of components contained in the present invention, a description will be given of bicarbonate which is represented by sodium bicarbonate.

Bicarbonate used in the present invention, in particular, sodium bicarbonate, functions as a bubble forming agent. When dissolved together with an organic acid in water ("hot water" is included in the present invention and the same shall apply hereinafter), while generating bubbles of carbon dioxide due to a neutralization reaction, the sodium bicarbonate is dissociated into bicarbonate ions and hydrogen ions, depending of a pH value of dissolved water, and dissolved in water. At this time, sodium bicarbonate facilitates dissolution of a chlorine neutralizing compound represented by sodium L-ascorbate contained together in the tablet in water. A content of sodium bicarbonate in the present invention is specified in relation to a mixture B which contains an organic acid and which will be described later. If the content of sodium bicarbonate is less than a specified content, a quantity of bubbles formed and a pH value on dissolution in water are not as per specified, and the effects of the present invention are not obtained and bicarbonate ions dissolved into water are significantly decreased in quantity. On the other hand, where the content thereof is in excess of the specified quantity, a pH value is made too high to significantly decrease bubbles of carbon dioxide gas, and the effects of the present invention are less likely to be exhibited.

Next, a description will be given of an organic acid represented by citric acid.

Any publicly known organic acid may be used as the organic acid of the present invention. In particular, citric acid reacts with bicarbonate much more remarkably than succinic acid and malic acid, functioning to neutralize the sodium bicarbonate and generate effectively bubbles of carbon dioxide gas, thereby giving cleaning effects and softening effects to skin when dissolved in water. However, as the organic acid of the present invention, citric acid, succinic acid, malic acid and fumaric acid are effective bubble forming materials. However, not only warm bath effects but also beauty promoting effects and others are varied in extent depending on the kind of organic acid, and citric acid is the best organic acid. The content thereof is specified as will be described later. If the content is less than the above described content, bubbles of carbon dioxide gas formed during dissolution of the tablet are decreased in quantity and dissolved bicarbonate ions are also decreased in quantity, thus resulting in a decrease of blood flow promoting effects and others. In excess of the above-described content, bubbles of carbon dioxide gas are increased in quantity but such a disadvantage is found that the bubbles are increased in diameter and the gas is less likely to be neutralized and dissolved bicarbonate ions are decreased in quantity.

Next, a description will be given of a chlorine neutralizing compound which is represented by L-ascorbic acid, L-ascorbate, sodium thiosulfate and sodium sulfite.

As ascorbic acid and ascorbate used in the present invention, those which are publicly known may be used without any special restrictions. Preferable salts include sodium salt and calcium salt. Sodium salt is more preferable in view of effects of the present invention.

L-ascorbic acid is widely known as vitamin C. And, when added to tap water, it removes chlorine contained in tap water through reactions shown by the reaction formulae 1, 2 given below.

[Reaction Formula 1]

(Reaction for reducing and removing sodium hypochlorite added for primary sterilization by ascorbic acid)

[Reaction Formula 2]

(Reaction for removing chlorine added for retaining chlorine concentrations by ascorbic acid)

When ascorbic acid of the present invention is dissolved in tap water via the reactions shown by the above-described Reaction Formulae 1, 2, chlorine contained in tap water is removed. Thereby, it is possible to prevent problems caused by residual chlorine to the skin and hair, that is, occurrence of "oxidation, aging, dandruff, eczema and itching." It is also possible to provide effects of an increase in smooth textured skin, prevention of fine wrinkles, beautiful skin care, fair skin care and anti-aging which are the efficacy of ascorbate in itself.

Further, as shown in Reaction Formula 2, hydrochloric acid will occur in a small quantity on removal of chlorine. Since pH of dissolved water is buffered by buffer effects of bicarbonate ions and an organic acid, water used in a shower or used in a bathtub will not be changed to an acid pH range. And, pH of tap water is stable.

On the other hand, when L-ascorbic acid or L-ascorbate contained in the present invention is less than 0.005 g/15 g tablet in content, an ability to remove chlorine may be decreased. In excess of 1.0 g/15 g tablet, it is more difficult to solidify the tablet, with the hardness being less than target hardness. It is also preferable that other chlorine neutralizing compounds used in the present invention are within the above-described range.

Next, a further description will be given of the bathing agent (tablet) used in the present invention.

The present invention is such that bicarbonate is granulated by using polyethylene glycol (hereinafter referred to as "PEG" from time to time) or others, thereafter, an organic acid (in particular, citric acid, succinic acid, malic acid, fumaric acid), etc., is mixed with PEG or granulated, they are mixed under conditions that each of them is kept within a fixed ratio, a body rendering agent of the present invention is added thereto to mold a tablet by compression molding, and the tablet is designed so that pH immediately after dissolution of the tablet will fall within a scope of the present invention, by which the tablet is allowed to react so as to generate bubbles of carbon dioxide gas intensively and uniformly when water permeates into the tablet, and also bubbles of carbon dioxide gas are generated for a prolonged period of time as microsized fine carbon dioxide gas, the tablet continues to generate microsize bubbles until the completion of the dissolution, and water is designed to be in a pH range of 5.5 to 9.0 so that bubbles are neutralized in water before being dissipated into air and dissociated into bicarbonate ions to give highly concentrated bicarbonate ions dissolved therein. Where the tablet is preferably in a pH range of 6.0 to 8.5 and particularly, in a pH range of 6.3 to 8.0, the effects of the present invention can be exhibited to the maximum extent.

Further, in the present invention, the mixture of bicarbonate is a granulated substance prepared by being coated with PEG by a fluidized bed. Thereby, the effects of the present invention such as continuous and uniform reactions in the tablet are exhibited to the maximum extent.

Still further, in the present invention, where the tablet is 15 kg or more in hardness, preferably 25 kg or more and particularly preferably 30 kg or more, that is, the higher the hardness, reactions of the chlorine neutralizing compound proceed more stably and continually. It is, therefore, preferable that the tablet is formed to be high in hardness so that the tablet can suppress a neutralization reaction of chlorine within the tablet and a dissolved portion of the tablet can quickly remove chlorine in hot water. The higher the chlorine removing effects are, the greater health promotion effects such as improvement of blood circulation and elevation of body temperature become even at the time of a shower.

Still further, in the present invention, where the present invention is 10.0 wt % or less in tablet friability, particularly preferably 5.0 wt % or less and more preferably 3.0 wt % or less, the lower the chlorine neutralizing compound undergoes continuously more stable reactions. Thereby, the neutralization reaction of chlorine within the tablet is not only made maximum in efficiency but also in the case of bathing in a bathtub or footbath and even in the case of taking a shower, there can be obtained health promoting effects such as improvement of blood circulation and elevation of body temperature.

The organic acid used in the present invention includes citric acid, fumaric acid, succinic acid and malic acid. In particular, where citric acid is used as the organic acid, it exhibits more remarkably the effects of the present invention as a preferable compound which suppresses a neutralization reaction in the tablet and increases an ability to remove chlorine in hot water, thereby generating fine bubbles of carbon dioxide gas.

Where at least one of bicarbonate and an organic acid is granulated by using a fluidized bed to obtain granulated substances, a mechanical fluidized bed granulating machine which does not substantially utilize air for agitation can be used to efficiently enhance reactions in the tablet. In the mechanical agitation type fluidized bed, upon agitation, no air is used for fluoridation but a mechanical blade such as a propeller is used to fluidize powder. In this case, the mechanical agitation type fluidized bed will not absorb moisture coming from wet air during granulation and is able to realize a vacuum during granulation by using a vacuum pump and carry out granulation, with PEG decreased in quantity. The above-described fluidized bed is thus able to exhibit the effects of making bubbles extremely small in diameter while further activating neutralization reactions. Therefore, it is used preferably.

The mechanical fluidized-bed granulating machine which does not substantially utilize air for agitation is preferably used, and this is a mixer in which a plow-like shovel is installed in a horizontal-type drum to cause centrifugation, diffusion and vortex actions, thereby effecting three-dimensional fluidization. The granulating machine of this type is marketed, for example, as one made by Gebrüder Lödige Maschinenbau GmbH in Germany or Matsuzaka Engineering Co., Ltd.

It is more preferable that the granulating machine is provided with a vacuum pump for reduction in pressure. That is, the machine can be operated so as to reduce pressure on cooling and remove moisture as much as possible thereby enhancing the effects of the present invention.

It is more preferable that the granulating machine is provided with a chopper for preventing granulated grains from becoming coarse particles on cooling. That is, the chopper is actuated on cooling to make particles uniform, thereby exhibiting the effects of the present invention, that is, bubbles of carbon dioxide gas are made smaller in microsize in diameter. And, this is a more preferable granulation method.

In the present invention, the most preferable production method is such that sodium bicarbonate is granulated together with PEG by using a fluidized bed granulating machine on the basis of a mechanical agitation method, an organic acid, anhydrous sodium carbonate and PEG are added at certain ratios to the thus prepared granulated substance and mixed, thereafter, they are subjected to compression molding at a high pressure, thereby giving a tablet.

As a matter of course, a mixture mainly composed of an organic acid is granulated by using PEG which is only mixed with PEG without granulation of bicarbonate, and a resultant thereof is then mixed with an organic-acid granulated substance and subjected to compression molding to prepare a tablet. This is also a preferable production method in view of a relatively smaller quantity of compounds used for granulation and steps involved therein. In any case, in view of cost, it is desirable that a tablet is manufactured by procedures in which one of bicarbonate and organic acid is granulated and the other is only mixed. Although the granulated substance which is used as it is, that is, as a powder agent can exhibit an ability to neutralize chlorine, it is subjected to compression molding and formed into a tablet, by which neutralization reactions of the present invention can be retained for a prolonged period of time and carbon dioxide gas which is dissolved can be increased. However, both of the bicarbonate and the organic acid may be used by being mixed with PEG or being coated, and this is also a preferable production method.

In the present invention, PEG with an average molecular weight of 1000 to 8000 is preferably used in exhibiting the effects of the present invention. When a compression molding tablet machine such as a rotary type tablet machine is used, PEG with an average molecular weight of about 4000 to 6000, particularly preferably, PEG with an average molecular weight of 6000 is able to provide preferable granulation results such as improvement in molding stability, rod attachment resistance, capping and tablet molding velocity. Therefore, where the tablet is dissolved in hot water, carbon dioxide gas components can be dissolved in a maximum quantity so as to give bicarbonate ions.

A ratio of PEG in relation to a mixture A (or a granulated substance A depending on a case) of bicarbonate (sodium hydrogen carbonate or potassium hydrogen carbonate) of 100 parts by mass is preferably from 1:100 to 1:5 and particularly preferably from 1:100 to 1:8. Where the ratio of PEG is smaller than the above-described ratio, it is difficult to obtain sufficiently high hardness or difficult to obtain sufficiently low friability, bubbles of carbon dioxide gas are increased in diameter and bubble generating time is shortened, thus resulting in a possible failure in increasing concentrations of bicarbonate ions dissolved in water. On the other hand, where the ratio of PEG is larger than the above-described ratio, generation of bubbles of carbon dioxide gas may be suppressed in quantity to also reduce a quantity of bicarbonate ions dissolved in water.

Further, in the present invention, in a step where the granulated substance A of bicarbonate or the mixture A of PEG has been obtained and thereafter, an organic acid, an organic-acid granulated substance B, or a PEG/organic-acid mixture B is added, an anhydride such as anhydrous sodium carbonate and anhydrous potassium carbonate is added, thus making it possible to exhibit the effects of the present invention more remarkably. And, such effects are obtained that bubbles of carbon dioxide gas are made small to a microsize in diameter, the bubbles are generated in a greater quantity and also kept generated for a prolonged period of time.

Where anhydrous sodium carbonate or anhydrous potassium carbonate is added as the above-described anhydride, there are exhibited more preferable effects of the present invention.

Further, in the present invention, where an organic acid is not made into a granulated substance but at least one of those selected from alkane sulfonate with a carbon number of 6 to 18, olefin sulfonate, sucrose fatty acid ester, sodium sulfate and magnesium sulfate is added to PEG together with an organic acid and only mixed together and a resultant thereof is compression-molded together with the mixture A to give a tablet, it has been found that microsize bubbles of the present invention can be generated for a prolonged period of time to facilitate dissolution of carbon dioxide gas components in hot water. Thereby, it is possible to obtain a favorable tablet. In this case, not only can steps be omitted to a great extent but also costs can be reduced, and therefore, this is a desirable production method.

On the other hand, even where an organic acid is mixed or granulated with PEG and at least one of those selected from alkane sulfonate with a carbon number of 6 to 18, olefin sulfonate, sucrose fatty acid ester, sodium sulfate and magnesium sulfate which is a body rendering agent of the present invention and a resultant thereof is mixed with the mixture A at a certain temperature and then subjected to compression molding, it is possible to obtain a tablet which generates microsize bubbles of the present invention for a prolonged period of time and facilitate dissolution of carbon dioxide gas components in water to the maximum extent and retain an ability to remove chlorine stably until the end. This is found to be a desirable production method.

In the above-described production method, it is preferable that PEG is used together with an organic acid in a range of 5 to 15 parts by mass in relation to the organic acid of 100 parts by mass.

The granulated substance B or the mixture B in relation to the granulated substance A of bicarbonate or the mixture A thereof is added in a range of 1:100 to 2:3, preferably in a range of 1:50 to 2:3 and particularly preferably in a range of 1:10 to 1:3.

Even if the organic acid is not in particular granulated, the effects of the present invention can be obtained by adding the above-described anhydride. It is, however, more preferable that the organic acid is added together with PEG or made into the granulated substance B, mixed with the granulated substance A and subjected to compression molding for giving a tablet. It is, thereby, possible to prepare a tablet having preferable neutralization reactions.

Further, in the present invention, it is preferable that the above-described anhydride is added in any one of steps upon compression molding, for example, a step in which the granulated substance A or the mixture A is prepared and a step in which the granulated substance A and the mixture B or the granulated substance B are mixed.

In the present invention, the body rendering agent used in mixing a powder agent or in molding a tablet includes sodium alkanesulfonate with a carbon number of 6 to 18, sodium olefin sulfonate with a carbon number of 6 to 18, sucrose fatty acid ester, sodium sulfate and magnesium sulfate. A compound which can be used desirably includes n-(normal) sodium octane sulfonate, sodium tetradecene sulfonate, a sodium alkane sulfonate mixture with a carbon number of 6 to 18, sucrose lauric acid ester, sucrose myristic acid ester, sucrose palmitic acid ester, sodium sulfate and magnesium sulfate. Of these substances, n-(normal) sodium octane sulfonate, sodium tetradecene sulfonate, and n-heptane sodium sulfonate are particularly preferably used in effectively attaining the object of the present invention.

In the above-described present invention, n-(normal) sodium octane sulfonate, sodium tetradecene sulfonate, and n-heptane sodium sulfonate are preferably added in a range of 1:10 to 1:1000 in relation to an organic acid used in the tablet according to the present invention. Other body rendering agents may be added in a similar quantity.

Sodium alkane sulfonate and sodium olefin sulfonate which are particularly preferable are those which contain at least one of a sodium alkane sulfonate mixture with a carbon number of 6 to 18, sodium tetradecene sulfonate and normal sodium octane sulfonate.

Sodium chloride, potassium chloride, desiccated sodium sulfate, magnesium sulfate, magnesium oxide, anhydrous silicic acid, sodium hydroxide, dextrin and calcium silicate are additives which exhibit the effects of the present invention, when added to the mixture B and the granulated substance B. In addition, flavors, pigments and surface-active agents are included as additives.

Any publicly known compression molding machine can be used without special restrictions in conducting compression molding for producing the tablet according to the present invention. For example, a hydraulic pressing machine, a single tablet machine, a rotary-type tablet machine and a briquetting machine may be used. A rod used in the tablet machine is preferably 7 mm or more in diameter when the rod is formed in a circular shape. Where the rod is formed in a triangle or rectangular shape, the rod is preferably 7 mm or more in diameter which is calculated on conversion to a circular rod. This also applies to the thickness of the rod. Where a circular tablet is prepared, the diameter of the tablet is desirably 7 mm or more and more desirably 10 mm or more, and the thickness thereof is also preferably 7 mm or more and more preferably 10 mm or more. Where the tablet is formed in a triangle or rectangular shape, the tablet is preferably 7 mm or more upon conversion to a circular tablet both in diameter and thickness and it is particularly preferably 10 mm or more.

As described above, the tablet of the present invention is not necessarily formed in a circular shape having a flat face. The tablet may be formed in an oval or spherical shape as long as it is a solid substance of 7 mm or more, with no restrictions on its shape of the tablet.

In the present invention, it is preferable that the tablet of the present invention is able to slowly generate microsize bubbles higher in hardness and friability as well as larger in size than a certain size and dissolve carbon dioxide gas more efficiently in hot water. Therefore, hardness of the tablet is 15 kg or more, desirably 25 kg or more and particularly preferably 35 kg or more. Friability of the tablet is also preferably 10.0 wt % or less, more preferably 5 wt % or less and particularly preferably 3 wt % or less. It is particularly preferable that the table is 10 mm or more both in diameter and thickness. Carbon dioxide gas is, thereby, generated more effectively in the tablet and dissolved effectively in water. And, bubbles are made fine in diameter, thereby attaining the object of the present invention effectively.

Hereinafter, a description will be given of hardness of the tablet in the present invention.

In order to implement the present invention, hardness of the tablet was measured in terms of tablet destruction strength in a diameter direction which is used in examples of a number of patent applications.

In the above-described measurement, the tablets were measured for destruction strength. As a method for measuring the hardness in the diameter direction, a digital tablet hardness tester, New Speed Checker TS75NL made by OKADA SEIKO CO., LTD. was used to measure the hardness of the tablets [kg] four times. In this case, the hardness was reproducible and no large variations in value were found.

The diameter of bubbles of carbon dioxide gas generated in hot water, that is, a preferable condition of the tablet of the present invention, was visually observed to find that bubbles were not joined together but generated consistently in the tablet with a diameter of 7 mm or more in particular in the tablet with a diameter of 10 mm or more. In order that the tablet continued to react until the completion of neutralization reactions and complete dissolution of the tablet, carbon dioxide gas was neutralized, thereby efficiently dissolving bicarbonate ions in hot water, 12 different samples of 7 lots of the tablets prepared on a trial basis were used to measure the hardness of the tablets. The measurement was made four times to obtain a mean value, thus making it possible to disregard a variation in measured values. It was confirmed that the tablets were 15 kg or more and in particular 25 kg or more in mean hardness.

Hereinafter, a description will be given of friability of the tablet according to the present invention. Tablets are put into a tablet friability tester (made by Kayagaki Irika Kogyo KK) so as to give a tablet weight of 31 g or more. For example, where one tablet weighs 15 g, three tablets are put therein and rotated for two minutes (the rotation rate of 25 rpm). Powder on a surface of each tablet after having been rotated is removed by using a brush (that used in cleaning a chemical balance, for example) (defacement), and the friability is determined by referring to the following formula.

[(Sum of tablet weight (g) before defacement−Sum of tablet weight (g) after defacement)]/Sum of tablet weight (g) before defacement]×100=Tablet friability (wt %).

For example, where one tablet weighs 40 g, one tablet is put therein and where one tablet weighs 60 g, one tablet is also put therein. Where one tablet weighs 16.5 g, two tablets are put therein.

Where the tablet is 10.0 wt % or less in friability, generation of microsize bubbles takes place slowly in the tablet, and dissolution of carbon dioxide gas in a liquid can be controlled efficiently. Therefore, the friability is to be 10.0 wt % or less, more preferably 5.0 wt % or less and particularly preferably 3.0 wt % or less. Where the tablet is within a range of the friability specified in the present invention, carbon dioxide gas is generated efficiently in the tablet in particular after start of dissolution of the tablet, and carbon dioxide gas is dissolved effectively in water to generate bubbles small in diameter. Thereby, the effects of the present invention are favorably realized.

In the present invention, it is desirable that compounds other than the compounds of the present invention are not added as much as possible. It is, however, possible to add one or two or more of different acid components, alkaline components, flavor or turbid spring components whenever necessary.

In the present invention, where a quantity of organic acid components in relation to bicarbonate exceeds a scope specified in the present invention, the bubbles are increased in diameter and reactions may become intense and terminate in a short period of time. Further, where a quantity of organic acid components in relation to bicarbonate is excessively small, neutralization reactions may not take place efficiently to generate carbon dioxide gas in a small quantity. The effects of the present invention may not be exhibited.

Further, where a quantity of bicarbonate is excessively small, PEG must be used in an increased quantity. Otherwise, neutralization reactions would become too intense and bubbles would be increased in diameter to spoil the effects of the present invention. Still further, where a quantity of PEG is excessively large or small in relation to bicarbonate and an organic acid, neutralization reactions may not take place uniformly and continuously or bubbles may not be uniform in diameter.

As described above, it is essentially important that components required by the present invention are added in a preferable ratio specified in the present invention, a pH adjusting agent is added so as to obtain sufficient effects of the present invention and an aqueous solution after dissolution is kept in a pH range specified in the present invention.

Sodium carbonate and an organic acid are preferably used as the pH adjusting agent of the present invention, and any other publicly known substances can be used without any special restrictions. The tablet may enter into the eyes and mouth and, therefore, a pH adjusting agent which is approved as a food additive is particularly preferably used in view of the safety. The agent includes, for example, trisodium citrate (sodium citrate), disodium citrate, monosodium citrate, potassium gluconate, sodium gluconate, disodium succinate, sodium acetate, DL-sodium tartrate, L-sodium tartrate, potassium carbonate, sodium hydrogen carbonate, sodium carbonate, sodium lactate, DL-sodium malate and others.

The present invention exhibits the effects of the present invention to the maximum extent where the micro-bubble production device is provided with a shower head portion and a shower body which are arranged integrally or arranged in a combined manner and the micro-bubble generating portion is disposed at any one of (1) to (6) which have been described previously.

Hereinafter, a detailed description will be given of the present invention by referring to examples and reference examples. Modes of the present invention shall not be, however, limited to these examples.

At first, Reference Examples 1 to 3 will be described.

Reference Example-1

Operation-1

Sodium hydrogen carbonate, 390 kg, was added to a modified type of Lödige mixer VT1200 made by Matsuzaka Engineering Co., Ltd., and the mixer was rotated at 115 rpm to circulate hot water with a temperature of 60° C. in a jacket. When a powder thereof reached a temperature of 55° C., PEG 6000 was added in a quantity of 20 kg and a resultant was granulated. When the powder reached a temperature of 58.5° C., cold water was circulated in the jacket and the mixer was reduced in pressure at 10 Torr, and cooling was performed until the powder reached a temperature of 45° C.

And, a granulated substance AA was obtained.

Operation-2

The granulated substance AA, 322 kg, anhydrous citric acid, 69 kg, anhydrous sodium carbonate, 19 kg, PEG 6000, 4.8 kg, sodium L-ascorbate, 2.8 kg, and n-octane sulfonic acid soda, 2 kg, were put into a modified type of Lödige mixer VT1200 and a resultant thereof was agitated at 115 rpm for 10 minutes to prepare a mixture AA.

Operation-3: Preparation of Tablet

The Tough Press Correct 1527HU (tablet machine) made by Kikusui Seisakusho Ltd. was used to apply a load of 12 tons to the mixture AA prepared by the above-described operation, thereby producing a tablet (1) with a diameter of 30 mm, thickness of 12 mm and weight of 15 g. The tablet (1) was 50 kg in hardness, 3.0 wt % in friability. And, pH of an aqueous solution prepared by dissolving one tablet at 25° C. in 1 L water was 7.00.

As shown in Table 1 given below, in the above operation, anhydrous citric acid (organic acid), sodium n-octane sulfonate and sodium L-ascorbate were changed in quantity or "free" to prepare tablets (2) to (4).

Tap water from a public water supply, 160 L, was put into a general household-use bathtub capable of boiling water, and the water was boiled at a set temperature of 39° C. and was set at 38° C. for keeping the temperature. At the same time when the water reached a temperature of 38° C., the tablets (1) to (4) prepared in the above operation were placed into the hot water, with three each used in each experiment. A commercially available digital residual chlorine meter HI96711 was used to measure concentrations of residual chloride of lime before the tablets was placed, thereby obtaining a result that residual chloride of lime of 5 mg/kg was detected. On the other hand, the same measurement was made one minute later to find that no residual chloride of lime was detected in any of the public tap water of 160 L. This revealed that the tablets have an ability to effectively remove residual chloride of lime. Tablets (1) to (4) were completely dissolved while generating bubbles in about 15 minutes after they were placed into the hot water.

Evaluation Method

Ten subjects (5 males and 5 females aged from 50 to 70, with an average age of 60.5) were measured for blood flow during a period of time from before taking a bath, during taking a bath and up to one hour after taking a bath by using a hematachometer, that is, a laser Doppler tissue blood flow meter ADVANCE ALF 21N (made by ADVANCE CO., LTD.). There was measured a site on the back of the hand corresponding to "so called Goukoku," a pressure spot of acupuncture. A measurement was made, with a measurement probe attached to the skin.

The blood flow measurement pattern is as follows. Resting state: 20 minutes (room temperature, 25° C.→bathing (38° C.): 20 minutes→after bathing, resting state (room temperature, 25° C.): 20 minutes, a total of 60 minutes

TABLE 1

| Experiment No. (Tablet No.) | Ratio of citric acid (organic acid) to sodium bicarbonate | Ratio of sodium n-octane sulfonate to citric acid | Ratio of sodium L-ascorbate to citric acid | Remarks |
|---|---|---|---|---|
| (1) | 0.23 | 0.03 | 0.04 | Present invention |
| (2) | 0.23 | 0.03 | 0 | Control (free of sodium L-ascorbate) |
| (3) | 0.68 | 0.03 | 0.04 | Control |
| (4) | 0.009 | 0.03 | 0.04 | Control |
| 5 | — | — | — | Control Newly boiled water |

FIG. 1 shows tissue blood flow volumes at the time of bathing which were measured according to the blood flow measurement pattern described above.

As apparent from FIG. 1, the present invention of Experiment No. 1 has increased blood flow about 6 times more than newly boiled water of Experiment No. 5 and about 2 times more than controls of Experiments No. 2, 3 and 4 when a bath is taken at a relatively low temperature of 38° C., and the effects of increasing blood flow are found even after bathing. This has demonstrated that when the bathing agent of the present invention is used in a state of para-sympathetic nerve predominance while bathing at a low-temperature, the effects of increasing blood flow are obtained very favorably.

Reference Example-2

In addition to the tablets (1) to (4) prepared in Reference Example-1, tablets (6) to (14), (15-1), (15-2), (15-3) and (15-4) were prepared according to the compositions shown in Table 2 in similar procedures to those of Reference Example-1. They were evaluated as follows.

Each measurement was made for a skin surface temperature on the instep of the foot immediately after complete dissolution of the tablets and before taking a bath (T1), a skin surface temperature on the instep of the foot after 20-minute bathing (T2) and a skin surface temperature on the instep of the foot after the elapse of one hour in an air-conditioned room kept at 25° C. after bathing (T3). The measurement was made by using a T0-400 non-contact infrared thermometer (the Ministry of Health, Labor and Welfare, License Number: 226AFBZX00131000).

Evaluation A

Arithmetic mean values of T2–T1 (a temperature obtained by deducting T1 from T2) in 10 subjects are:
5: Temperature of 0.8° C. or more is elevated.
4: Temperature of 0.6 or more to less than 0.8° C. is elevated.
3: Temperature of 0.4 or more to less than 0.6° C. is elevated.
2: Temperature of 0.2 or more to less than 0.4° C. is elevated.
1: Temperature of less than 0.2° C. is elevated.

Evaluation B

Arithmetic mean values of T3–T2 (a temperature obtained by deducting T2 from T3) in 10 subjects are:
5: Temperature of less than 0.2° C. is lowered.
4: Temperature of 0.2 or more to less than 0.4° C. is lowered.
3: Temperature of 0.4 or more to less than 0.6° C. is lowered.
2: Temperature of 0.6 or more to less than 0.8° C. is lowered.
1: Temperature of 0.8° C. or more is lowered.

TABLE 2

| Experiment No. (Tablet No.) | Ratio of citric acid (organic acid) to sodium bicarbonate | Ratio of sodium n-octane sulfonate to citric acid | Ratio of sodium L-ascorbate to citric acid | Evaluation A | Evaluation B | Remarks |
|---|---|---|---|---|---|---|
| (1) | 0.23 | 0.03 | 0.04 | 5 | 5 | Present invention |
| (2) | 0.23 | 0.03 | — | 2 | 1 | Control (free of sodium L-ascorbate) |
| (3) | 0.68 | 0.03 | 0.00 | 1 | 1 | Control |
| (4) | 0.009 | 0.03 | 0.04 | 2 | 1 | Control |
| 5 | — | — | — | 1 | 1 | Control Newly boiled water |
| (6) | 0.02 | 0.03 | 0.04 | 4 | 4 | Present invention |
| (7) | 0.01 | 0.03 | 0.04 | 3 | 3 | Present invention |
| (8) | 0.66 | 0.03 | 0.04 | 4 | 4 | Present invention |
| (9) | 0.23 | 0.001 | 0.04 | 4 | 3 | Present invention |
| (10) | 0.23 | 0.008 | 0.04 | 5 | 4 | Present invention |
| (11) | 0.23 | 0.1 | 0.04 | 4 | 4 | Present invention |
| (12) | 0.23 | 0.11 | 0.04 | 3 | 2 | Control |
| (13) | 0.23 | 0.03 | 0.01 | 4 | 4 | Present invention |
| (14) | 0.23 | 0.03 | 0.008 | 4 | 3 | Present invention |
| (15-1) | 0.23 | 0.03 | 0.08 | 4 | 4 | Present invention |
| (15-2) | 0.23 | 0.03 | 0.05 | 5 | 5 | Present invention |
| (15-3) | 0.23 | 0.03 | 0.082 | 3 | 2 | Control |
| (15-4) | 0.23 | 0.0009 | 0.04 | 2 | 2 | Control |

Table 2 has revealed that the present invention provides favorable results of increase in blood flow when a bath is taken at a low temperature. It has also been revealed that the effects of a sensory evaluation are more apparent than those of the measurement of tissue blood flow.

Reference Example-3

In Experiment No. 1 of Reference Example-1, a load and tablet making speed in Operation-3 were changed whenever necessary to prepare tablets (16) to (20) different in friability as shown in Table 3. When dissolved in hot water, pH of the tablets (16) to (20) was 7.0.

T1, T2 and T3 shown in Reference Example-2 were measured to determine values of Evaluation A and Evaluation B. And, the results are shown in Table 3.

TABLE 3

| Experiment No. | Friability (wt %) | Evaluation A | Evaluation B | Remarks |
|---|---|---|---|---|
| (1) | 3.0 | 5 | 5 | Present invention |
| (16) | 10.2 | 3 | 3 | Reference |
| (17) | 10.0 | 4 | 4 | Present invention |
| (18) | 5.2 | 4 | 4 | Present invention |
| (19) | 5.0 | 5 | 4 | Present invention |
| (20) | 3.2 | 5 | 4 | Present invention |

As apparent from Table 3, when the friability is 10 wt % or less, the effects of the present invention can be obtained, and the friability is preferably 5.0 wt % or less and more preferably 3.0 wt %.

Experiment results shown in Reference Examples 1 to 3 were also found in experiments in showering shown in Example 1 and subsequent examples given below.

Hereinafter, a description will be given of examples of the present invention.

Example-1

Tablets (21) to (33) were prepared according to the compositions shown in Table 4-(2) in the same way as Reference Example-1. These tablets were used to conduct the following experiment in showering.

The tablets were set in a shower head shown in FIG. 1 of Japanese Utility Model Registration No. 3190347, and a pump-equipped system was provided so that a shower of tap water from a public water supply was fed from a 100-liter container heated at 40° C. (container free from change in chlorine content).

Residual chlorine in the tap water from a public water supply heated at 40° C. (Tokyo Metropolitan Government Bureau of Waterworks: water pressure, 3.5 kgf/cm$^2$) was determined for a concentration according to JIS K 0102: 2008 33.4 (diphenyl-p-phenylene diammonium (DPD) absorption spectrophotometry) by using an ultraviolet and visible spectrophotometer V-650 made by JASCO Corporation. The concentration was adjusted to 0.5 mg/L (0.5 ppm) by using commercially available sodium hypochlorite.

(A-1) Evaluation of Chlorine Neutralizing Ability—Part 1

The above-described solution was used to measure concentrations of residual chlorine in hot water from a shower immediately after the tablet starts to dissolve by DPD absorption spectrophotometry. The results are shown in Table 4-(1). A value of less than 0.05 in the table shows that it is lower than a determination limit in this analysis.

(A-2) Evaluation of Chlorine Neutralizing Ability—Part 2

It has been confirmed that the tablet was completely dissolved in 7 minutes. Thus, hot water from a shower was collected after 6 minutes 30 seconds from start of the dissolution which is immediately before the completion of dissolution and similarly measured for concentrations of residual chlorine. The results are shown in Table 4-(1).

Evaluations (B) to (E) given below are arithmetic mean values obtained from the 10 subjects.

(B) Hair root mineral dirt: "hair root mineral dirt" is dirt in which mineral ions of calcium, magnesium, copper, etc., (ions contained in tap water) attached to surfaces of protein, keratin, etc., of the scalp and hair to effect ionic bonding adhere and accumulate in hair roots at high concentrations. The evaluation was made by macroscopic observation using a loupe with a magnification of 5× (based on Evaluation 5 in which dirt is removed at 100%).

Evaluation 1: hair root mineral dirt is not removed at all.
Evaluation 2: hair root mineral dirt is removed less than 20%.
Evaluation 3: hair root mineral dirt is removed from 20% or more to less than 50%.
Evaluation 4: hair root mineral dirt is removed from 50% or more to less than 80%.
Evaluation 5: hair root mineral dirt is removed from 80% or more to 100%.

(C) Warmness of toes after the elapse of 30 minutes from washing of hair: a change in color of the skin was observed by using a thermography TVS500IS (on the basis of Evaluation 5 in which a change in color of the skin is 100%)

Evaluation 1: less than 10%
Evaluation 2: from 10% or more to less than 20%
Evaluation 3: from 20% or more to less than 50%
Evaluation 4: from 50% or more to less than 80%
Evaluation 5: from 80% or more to 100%

(D) A sleep meter HSL-101 made by OMRON Corporation was used to evaluate the percentage of sound sleeping hours.

Evaluation 1: sound sleeping hours, less than 10%
Evaluation 2: sound sleeping hours, from 10% or more to less than 20%
Evaluation 3: sound sleeping hours, from 20% or more to less than 40%
Evaluation 4: sound sleeping hours, from 40% or more to less than 50%
Evaluation 5: sound sleeping hours, 50% or more (E) "Memoret" or a lens marketed by Hada more was used to take images, and an evaluation was made for skin dullness-free clear fair skin in terms of an area on the basis of the following evaluation (on the basis of Evaluation 5 in which the degree of fair skin is 100%)

Evaluation 1: an image in its entirety looks dull and no clear skin is found (degree of fair skin, from 0% to less than 20%)
Evaluation 2: an image is substantially dull and no clear skin is found (degree of fair skin, from 20% or more to less than 40%)
Evaluation 3: an image is decreased in dullness and clear skin is found (degree of fair skin, from 40% or more to less than 60%)
Evaluation 4: the skin is evaluated to be clear (degree of fair skin, from 60% or more to less than 80%)
Evaluation 5: the skin is clear and completely free of dullness (degree of fair skin, from 80% or more to 100%)

The above evaluation results of (B) to (E) were shown in Table 4-(2).

TABLE 4-(1)

| Experiment No. (Sample No.) | (A-1) Residual chlorine concentration (mg/mL) immediately after start of dissolution | (A-2) Residual chlorine concentration (mg/mL) immediately before completion of dissolution | Remarks |
|---|---|---|---|
| (21) | Less than 0.05 | Less than 0.05 | Present invention |
| (22) | Less than 0.05 | Less than 0.05 | Present invention |
| (23) | Less than 0.05 | 0.25 | Present invention |
| (24) | Less than 0.05 | 0.39 | Control |
| (25) | Less than 0.05 | Less than 0.05 | Present invention |
| (26) | Less than 0.05 | 0.38 | Control |
| (27) | Less than 0.05 | Less than 0.05 | Present invention |
| (28) | Less than 0.05 | 0.25 | Present invention |
| (29) | Less than 0.05 | Less than 0.05 | Present invention |
| (30) | Less than 0.05 | 0.24 | Present invention |
| (31) | Less than 0.05 | Less than 0.05 | Present invention |
| (32) | Less than 0.05 | 0.22 | Present invention |
| (33-1) | Less than 0.05 | Less than 0.05 | Present invention |
| (33-2) | Less than 0.05 | 0.39 | Control |

TABLE 4-(2)

| Experiment No. (Tablet No.) | Ratio of citric acid (organic acid) to sodium bicarbonate | Ratio of n-octane sulfonate to citric acid | Ratio of sodium L-ascorbate to citric acid | (B) Hair root mineral dirt | (C) Warmness of toes after washing | (D) Sound sleeping hours | (E) Fair skin (dullness-free and clear skin) | Remarks |
|---|---|---|---|---|---|---|---|---|
| (21) | 0.23 | 0.03 | 0.04 | 5 | 5 | 5 | 5 | Present invention |
| (22) | 0.02 | 0.03 | 0.04 | 4 | 4 | 4 | 5 | Present invention |
| (23) | 0.01 | 0.03 | 0.04 | 3 | 3 | 3 | 3 | Present invention |
| (24) | 0.009 | 0.03 | 0.04 | 2 | 2 | 2 | 2 | Control |
| (25) | 0.66 | 0.03 | 0.04 | 5 | 5 | 5 | 5 | Present invention |
| (26) | 0.68 | 0.03 | 0.04 | 2 | 2 | 2 | 2 | Control |
| (27) | 0.23 | 0.001 | 0.04 | 3 | 3 | 3 | 3 | Present invention |
| (28) | 0.23 | 0.008 | 0.04 | 5 | 5 | 5 | 5 | Present invention |
| (29) | 0.23 | 0.05 | 0.04 | 5 | 5 | 5 | 5 | Present invention |
| (30) | 0.23 | 0.051 | 0.04 | 5 | 5 | 5 | 5 | Present invention |
| (31) | 0.23 | 0.03 | 0.01 | 5 | 5 | 5 | 4 | Present invention |
| (32) | 0.23 | 0.03 | 0.008 | 3 | 3 | 3 | 3 | Present invention |
| (33-1) | 0.23 | 0.03 | 0.08 | 5 | 5 | 5 | 5 | Present invention |
| (33-2) | 0.23 | 0.0009 | 0.04 | 2 | 2 | 2 | 2 | Control |

The tablet No. 21 has the same components as the tablet (1) of Reference Example-1 but is different in details of the experiment and, therefore, given a new number. The same shall apply hereinafter.

As shown in Table 4-(1), only where the tablet is within a scope specified in the present invention, residual chlorine can be decreased in concentration to a very low level from immediately after start of dissolution of the tablet to immediately before the completion of the dissolution.

As apparent from Table 4-(2), only where the tablet is within a scope specified in the present invention, all the effects such as removal of hair root mineral dirt, warmness of toes after washing, sound sleeping hours and fair skin are obtained. On the other hand, where the tablet is out of a scope specified in the present invention, the tablet is decreased in chlorine removing functions, giving a small influence to other evaluation of performance.

Example-2

Example-2 was evaluated in the same way as Example-1 except that sodium n-octane sulfonate used in "Operation-2" of Reference Example-1 was changed to sodium alkane sulfonate with the carbon numbers described in Table 5. And, the results are shown in Table 5-(1) and Table 5-(2).

TABLE 5-(1)

| Experiment No. (Sample No.) | (A-1) Residual chlorine concentration (mg/mL) immediately after start of dissolution | (A-2) Residual chlorine concentration (mg/mL) immediately before completion of dissolution | Remarks |
|---|---|---|---|
| (34) | Less than 0.05 | Less than 0.05 | Present invention |
| (35) | Less than 0.05 | 0.37 | Control |
| (36) | Less than 0.05 | Less than 0.05 | Present invention |
| (37) | Less than 0.05 | Less than 0.05 | Present invention |
| (28) | Less than 0.05 | Less than 0.05 | Present invention |
| (39) | Less than 0.05 | 0.38 | Control |

TABLE 5-(2)

| Experiment No. (Tablet No.) | Carbon number of sodium alkane sulfonate | Ratio of citric acid (organic acid) to sodium bicarbonate | Ratio of n-octane sulfonate to citric acid | Ratio of sodium L-ascorbate to citric acid | (B) Hair root mineral dirt | (C) Warmness of toes after washing | (D) Sound sleeping hours | (E) Fair skin (dullness-free and clear skin) | Remarks |
|---|---|---|---|---|---|---|---|---|---|
| (34) | 8 | 0.23 | 0.03 | 0.04 | 5 | 5 | 5 | 5 | Present invention |
| (35) | 5 | 0.23 | 0.03 | 0.04 | 2 | 2 | 2 | 2 | Control |
| (36) | 6 | 0.23 | 0.03 | 0.04 | 4 | 4 | 4 | 5 | Present invention |
| (37) | 10 | 0.23 | 0.03 | 0.04 | 5 | 5 | 5 | 5 | Present invention |
| (38) | 18 | 0.23 | 0.03 | 0.04 | 4 | 4 | 4 | 2 | Present invention |
| (39) | 19 | 0.23 | 0.03 | 0.04 | 2 | 2 | 2 | 2 | Control |

As shown in Table 5-(1), only where the tablet is within a scope specified in the present invention, residual chlorine can be decreased in concentration to a very low level from immediately after start of dissolution of the tablet to immediately before the completion of the dissolution.

Table 5-(2) has revealed that alkane sulfonic acid with a carbon number of 6 to 14 of the present invention is effective in attaining all the effects such as removal of hair root mineral dirt, warmness of toes after washing, sound sleeping hours and fair skin. Alkane sulfonic acid with a carbon number of 8 or more is also found to be more preferable.

Example-3

In Experiment No. 1 of Reference Example-1, citric acid, sodium carbonate and sodium bicarbonate were changed in quantity to prepare tablets so as to give pH values shown in Table 6. A load of 7 tons in Operation-3 was also changed, whenever necessary, to prepare tablets different in hardness. The results including evaluation results are shown in Table 6-(1) and Table 6-(2). However, the friability was made equal to the friability of Reference Example-1 by changing a maximum loading time on making tablets.

TABLE 6-(1)

| Experiment No. (Sample No.) | (A-1) Residual chlorine concentration (mg/mL) immediately after start of dissolution | (A-2) Residual chlorine concentration (mg/mL) immediately before completion of dissolution |
|---|---|---|
| (40) | Less than 0.05 | Less than 0.05 |
| (41) | Less than 0.05 | 0.18 |
| (42) | Less than 0.05 | 0.14 |
| (43) | Less than 0.05 | 0.14 |
| (44) | Less than 0.05 | 0.08 |
| (45) | Less than 0.05 | 0.08 |
| (46) | Less than 0.05 | 0.10 |
| (47) | Less than 0.05 | 0.10 |
| (48) | Less than 0.05 | 0.18 |
| (49) | Less than 0.05 | 0.08 |
| (50) | Less than 0.05 | 0.14 |

As shown in Table 6-(1), only where the tablet is within a scope specified in the present invention, residual chlorine can be decreased in concentration to a very low level from immediately after start of dissolution of the tablet to immediately before the completion of the dissolution.

As apparent from Table 6-(2), the effects of the present invention are obtained favorably where pH of the tablet is from 5.5 to 8.5, more preferably in a pH range of 6.2 to 8.0 and particularly preferably in a range of 6.3 to 8.0. It has also been found that the hardness of the tablet which is less than 15 kg influences the effects of the present invention. The effects of the present invention are obtained where a pH value is up to 9.0.

Example-4

Except for changing the sodium n-octane sulfonate in "Operation-2" of Reference Example-1 to sodium tetradecene sulfonate, tablets were prepared in the same way as Reference Example-1 and an evaluation was made in the same way as Example-1. The results are shown in Table 7-(1) and Table 7-(2).

TABLE 7-(1)

| Experiment No. (Sample No.) | (A-1) Residual chlorine concentration (mg/mL) immediately after start of dissolution | (A-2) Residual chlorine concentration (mg/mL) immediately before completion of dissolution |
|---|---|---|
| (51) | Less than 0.05 | Less than 0.05 |
| (52) | Less than 0.05 | Less than 0.05 |

TABLE 6-(2)

| Experiment No. (Tablet No.) | pH value | Tablet hardness | (B) Hair root mineral dirt | (C) Warmness of toes after washing | (D) Sound sleeping hours | (E) Fair skin (dullness-free and clear skin) |
|---|---|---|---|---|---|---|
| (40) | 7.4 | 50 | 5 | 5 | 5 | 5 |
| (41) | 5.4 | 50 | 4 | 4 | 4 | 4 |
| (42) | 5.5 | 50 | 4 | 4 | 4 | 4 |
| (43) | 6.2 | 50 | 4 | 4 | 4 | 4 |
| (44) | 6.3 | 50 | 5 | 5 | 5 | 5 |
| (45) | 8.0 | 50 | 5 | 5 | 5 | 5 |
| (46) | 8.2 | 50 | 4 | 4 | 5 | 5 |
| (47) | 8.5 | 50 | 4 | 4 | 5 | 5 |
| (48) | 9.0 | 50 | 4 | 3 | 4 | 4 |
| (49) | 7.0 | 15 | 4 | 4 | 5 | 5 |
| (50) | 7.0 | 14 | 4 | 3 | 4 | 4 |

TABLE 7-(2)

| Experiment No. (Tablet No.) | Ratio of citric acid (organic acid) to sodium bicarbonate | Ratio of n-octane sulfonate to citric acid | Ratio of sodium L-ascorbic to citric acid | (B) Hair root mineral dirt | (C) Warmness of toes after washing | (D) Sound sleeping hours | (E) Fair skin (dullness-free and clear skin) |
|---|---|---|---|---|---|---|---|
| (51) | 0.23 | 0.03 | 0.04 | 5 | 5 | 5 | 5 |
| (52) | 0.23 | 0.03 | 0.04 | 4 | 4 | 4 | 5 |

As shown in Table 7-(1), only where the tablet is within a scope specified in the present invention, residual chlorine can be decreased in concentration to a very low level from immediately after start of dissolution of the tablet to immediately before the completion of the dissolution.

As shown in Table 7-(2), sodium tetradecene sulfonate provides results substantially similar to those of sodium alkane sulfonate, with the effects of the present invention obtained.

Example-5

Operation-4

Sodium hydrogen carbonate, 306 kg, and sodium ascorbate, 2.8 kg, were added to a modified type of Lödige mixer VT1200 made by Matsuzaka Engineering Co., Ltd., and the mixer was rotated at 115 rpm to circulate hot water at 60° C. in a jacket. When a powder reached a temperate of 55° C., PEG 6000 was added in a quantity of 15.7 kg and a resultant was granulated. When the powder reached a temperature of 58.5° C., cold water was circulated in the jacket and the mixer was reduced in pressure at 10 Torr, and cooling was performed until the powder reached a temperature of 45° C.

A granulated substance BB was obtained.

Operation-5

The granulated substance BB, 322 kg, anhydrous citric acid, 69 kg, anhydrous sodium carbonate, 19 kg, PEG 6000, 4.8 kg, and sodium n-octane sulfonate, 2 kg, were put into a modified type of Lödige mixer VT1200 and a resultant thereof was agitated at 115 rpm for 10 minutes to prepare a mixture BB.

Operation-6: Preparation of Tablets

The Tough Press Correct 1527HU (tablet machine) made by Kikusui Seisakusho Ltd. was used to apply a load of 7 tons to the mixture BB prepared by the above-described operation, thereby producing a tablet with a diameter of 30 mm, thickness of 15 mm and weight of 15 g. The tablet was 50 kg in hardness, 2.4 wt % in friability. And, pH of an aqueous solution by dissolution (tap water) was 7.00.

An evaluation was made in the same way as Example-1. The results are shown in Table 8-(1) and Table 8-(2).

TABLE 8-(1)

| Experiment No. (Sample No.) | (A-1) Residual chlorine concentration (mg/mL) immediately after start of dissolution | (A-2) Residual chlorine concentration (mg/mL) immediately before completion of dissolution |
|---|---|---|
| (53) | Less than 0.05 | Less than 0.05 |
| (54) | Less than 0.05 | Less than 0.05 |

TABLE 8-(2)

| Experiment No. (Tablet No.) | Ratio of citric acid (organic acid) to sodium bicarbonate | Ratio of n-octane sulfonate to citric acid | Ratio of L-ascorbic acid to citric acid | (B) Hair root mineral dirt | (C) Warmness of toes after washing | (D) Sound sleeping hours | (E) Fair skin (dullness-free and clear skin) |
|---|---|---|---|---|---|---|---|
| (53) | 0.23 | 0.03 | 0.04 | 5 | 5 | 5 | 5 |
| (54) | 0.23 | 0.03 | 0.04 | 5 | 5 | 5 | 5 |

As shown in Table 8-(1), only where the tablet is within a scope specified in the present invention, residual chlorine can be decreased in concentration to a very low level from immediately after start of dissolution of the tablet to immediately before the completion of the dissolution.

Table 8-(2) has revealed that the same effects of the invention can be obtained, regardless of whether the components are added to a granulated substance or a mixture, if added in the same quantity.

Example-6

Except for replacing the sodium L-ascorbate in "Operation-2" of Reference Example-1 with sodium sulfite and sodium thiosulfate, tablets were prepared in the same way as Reference Example-1. An evaluation was made in the same way as Example-1 and the results are shown in Table 9-(1) and Table 9-(2). The friability is 3.0 wt %.

TABLE 9-(1)

| Experiment No. (Sample No.) | (A-1) Residual chlorine concentration (mg/mL) immediately after start of dissolution | (A-2) Residual chlorine concentration (mg/mL) immediately before completion of dissolution |
|---|---|---|
| (55) | Less than 0.05 | Less than 0.05 |
| (56) | Less than 0.05 | Less than 0.05 |
| (57) | Less than 0.05 | Less than 0.05 |

TABLE 9-(2)

| Experiment No. (Tablet No.) | Chlorine neutralizing compounds | Ratio of citric acid (organic acid) to sodium bicarbonate | Ratio of n-octane sulfonate to citric acid | Ratio of L-ascorbic acid to citric acid | (B) Hair root mineral dirt | (C) Warmness of toes after washing | (D) Sound sleeping hours | (E) Fair skin (dullness-free and clear skin) |
|---|---|---|---|---|---|---|---|---|
| (55) | Sodium L-ascorbate | 0.23 | 0.03 | 0.04 | 5 | 5 | 5 | 5 |
| (56) | Sodium bicarbonate | 0.23 | 0.03 | 0.04 | 4 | 5 | 5 | 4 |
| (57) | Sodium thiosulfate | 0.23 | 0.03 | 0.04 | 4 | 5 | 5 | 5 |

As shown in Table 9-(1), only where the tablet is within a scope specified in the present invention, residual chlorine can be decreased in concentration to a very low level from immediately after start of dissolution of the tablet to immediately before the completion of the dissolution.

Table 9-(2) has revealed that sodium sulfite and sodium thiosulfate also exhibit the effects of the present invention. An experiment in which sodium sulfite was replaced by erythobic acid or sodium erythorbate exhibited the same results as sodium sulfite.

Example-7

Except for replacing the citric acid in "Operation-2" of Reference Example-1 with succinic acid, fumaric acid and malic acid, tablets were prepared in the same way as Reference Example-1 and an evaluation was made in the same way as Example-1. The results are shown in Table 10-(1) and Table 10-(2).

TABLE 10-(1)

| Experiment No. (Sample No.) | (A-1) Residual chlorine concentration (mg/mL) immediately after start of dissolution | (A-2) Residual chlorine concentration (mg/mL) immediately before completion of dissolution |
|---|---|---|
| (58) | Less than 0.05 | Less than 0.05 |
| (59) | Less than 0.05 | Less than 0.05 |
| (60) | Less than 0.05 | Less than 0.05 |
| (61) | Less than 0.05 | Less than 0.05 |

As shown in Table 10-(1), only where the tablet is within a scope specified in the present invention, residual chlorine can be decreased in concentration to a very low level from immediately after start of dissolution of the tablet to immediately before the completion of the dissolution.

Table 10-(2) has revealed that, of organic acids, citric acid is most preferable in view of the effects of the present invention.

Example-8

Except for changing the sodium L-ascorbate in "Operation-2" of Reference Example-1 to potassium ascorbate, calcium ascorbate, erythobic acid and sodium erythobate, and n-octane sulfonic acid was changed to sodium alkane sulfonate with a carbon number of 4 and 18 and sodium lauryl sulfate (refer to Table 11), tablets were prepared in the same way as Reference Example-1, and a shower was used in the same way as Example-1. Concentrations of residual chlorine in a shower ejection liquid were measured when the tablet was placed, consumed by 50%, consumed by 90% and completely dissolved. The results are shown in Table 11. The friability was to be 3.0 wt %.

Table 11 given below has revealed that the effects of the present invention are obtained.

TABLE 10-(2)

| Experiment No. (Tablet No.) | Organic acid | Ratio of citric acid (organic acid) to sodium bicarbonate | Ratio of n-octane sulfonate to citric acid | Ratio of sodium L-ascorbate to citric acid | (B) Hair root mineral dirt | (C) Warmness of toes after washing | (D) Sound sleeping hours | (E) Fair skin (dullness-free and clear skin) |
|---|---|---|---|---|---|---|---|---|
| (58) | Citric acid | 0.23 | 0.03 | 0.04 | 5 | 5 | 5 | 5 |
| (59) | Succinic acid | 0.23 | 0.03 | 0.04 | 4 | 5 | 4 | 4 |
| (60) | Fumaric acid | 0.23 | 0.03 | 0.04 | 4 | 5 | 4 | 4 |
| (61) | Malic acid | 0.23 | 0.03 | 0.04 | 4 | 5 | 4 | 4 |

TABLE 11

| Experiment No. (Tablet No.) | Chlorine neutralizing compounds | Lubricant | ① When tablet was placed | ② When tablet was consumed by 50% | ③ When tablet was consumed by 90% | ④ When tablet was completely dissolved | Remarks |
|---|---|---|---|---|---|---|---|
| (62) | Sodium L-ascorbate | Sodium n-octane sulfonate | Less than 0.05 | Less than 0.05 | Less than 0.05 | Less than 0.05 | Present invention |
| (63) | Potassium L-ascorbate | Sodium n-octane sulfonate | Less than 0.05 | Less than 0.05 | Less than 0.05 | Less than 0.05 | Present invention |
| (64) | Calcium L-ascorbate | Sodium n-octane sulfonate | Less than 0.05 | Less than 0.05 | Less than 0.05 | Less than 0.05 | Present invention |
| (65) | Erythorbic acid | Sodium n-octane sulfonate | Less than 0.05 | Less than 0.05 | Less than 0.05 | Less than 0.05 | Present invention |
| (66) | Sodium erythorbate | Sodium n-octane sulfonate | Less than 0.05 | Less than 0.05 | Less than 0.05 | Less than 0.05 | Present invention |
| (67) | Sodium L-ascorbate | C-4 sodium alkane sulfonate | Less than 0.05 | 0.3 ppm | 0.3 ppm | 0.3 ppm | Control |
| (68) | Sodium L-ascorbate | C-19 sodium alkane sulfonate | Less than 0.05 | 0.3 ppm | 0.3 ppm | 0.3 ppm | Control |
| (69) | Sodium L-ascorbate | Lauryl sulfonic acid soda | Less than 0.05 | 0.3 ppm | 0.3 ppm | 0.3 ppm | Control |
| (70) | Sodium L-ascorbate | Decene sulfonic acid soda | Less than 0.05 | Less than 0.05 | Less than 0.05 | Less than 0.05 | Present invention |
| (71) | Free | Sodium n-octane sulfonate | 0.3 ppm | 0.3 ppm | 0.3 ppm | 0.3 ppm | Control |

Except for changing the "sodium L-ascorbate" in "Operation-2" of Reference Example-1 was changed to "L-ascorbic acid," an experiment was conducted in the same way as Experiment No. 62. The same effects as those of No. 65 were obtained.

Example-9

Except that a mortar and a rod different from those used in Operation-3 of Reference Example-1 were used to change the thickness and diameter of the tablet as found in Table 12, an evaluation was made in the same way as Example-8. The results are shown in Table 12. The friability was to be 3.0 wt %.

As shown in Table 12 given below, only where the tablet is within a scope specified in the present invention, residual chlorine can be decreased in concentration to a very low level from immediately after start of dissolution of the tablet to complete dissolution thereof.

Further, it has been found that in the present invention, the tablet thickness is more preferably from 10 mm to 15 mm, and the tablet diameter is more preferably from 25 mm to 35 mm.

TABLE 12

| Experiment No. (Tablet No.) | Chlorine neutralizing compounds | Lubricant | Tablet thickness (mm) | Tablet diameter (mm) | ① When tablet was placed | ② When tablet was consumed by 50% | ③ When tablet was consumed by 90% | ④ When tablet was completely dissolved |
|---|---|---|---|---|---|---|---|---|
| (72) | Sodium L-ascorbate | Sodium n-octane sulfonate | 12 | 30 | Less than 0.05 | Less than 0.05 | Less than 0.05 | Less than 0.05 |
| (73) | Sodium L-ascorbate | Sodium n-octane sulfonate | 7 | 30 | 0.1 ppm | Less than 0.05 | Less than 0.05 | 0.1 ppm |
| (74) | Sodium L-ascorbate | Sodium n-octane sulfonate | 9 | 30 | 0.1 ppm | Less than 0.05 | Less than 0.05 | 0.1 ppm |
| (75) | Sodium L-ascorbate | Sodium n-octane sulfonate | 10 | 30 | Less than 0.05 | Less than 0.05 | Less than 0.05 | Less than 0.05 |
| (76) | Sodium L-ascorbate | Sodium n-octane sulfonate | 15 | 30 | Less than 0.05 | Less than 0.05 | Less than 0.05 | Less than 0.05 |
| (77) | Sodium L-ascorbate | Sodium n-octane sulfonate | 16 | 30 | 0.1 ppm | Less than 0.05 | Less than 0.05 | 0.1 ppm |
| (78) | Sodium L-ascorbate | Sodium n-octane sulfonate | 12 | 7 | 0.1 ppm | Less than 0.05 | Less than 0.05 | 0.1 ppm |
| (79) | Sodium L-ascorbate | Sodium n-octane sulfonate | 12 | 24 | 0.1 ppm | Less than 0.05 | Less than 0.05 | 0.1 ppm |
| (80) | Sodium L-ascorbate | Sodium n-octane sulfonate | 12 | 25 | Less than 0.05 | Less than 0.05 | Less than 0.05 | Less than 0.05 |
| (81) | Sodium L-ascorbate | Sodium n-octane sulfonate | 12 | 35 | Less than 0.05 | Less than 0.05 | Less than 0.05 | Less than 0.05 |
| (82) | Sodium L-ascorbate | Sodium n-octane sulfonate | 12 | 36 | 0.1 ppm | Less than 0.05 | Less than 0.05 | 0.1 ppm |

Example-10

In Experiment No. 1 of Reference Example-1, a load of 7 tons in Operation-3 was changed, whenever necessary, to prepare tablets different in hardness. An evaluation was made in the same way as Example 9. The results are shown in Table 13. Loading time of a maximum load on making tablets was changed to give the friability of 3.0 wt %.

TABLE 13

| Experiment No. (Tablet No.) | Hardness (kg) | ① When tablet was placed (ppm) | ② When tablet was consumed by 50% | ③ When tablet was consumed by 90% | ④ When tablet was completely dissolved |
|---|---|---|---|---|---|
| (83) | 60 | Less than 0.05 | Less than 0.05 | Less than 0.05 | Less than 0.05 |
| (84) | 50 | Less than 0.05 | Less than 0.05 | Less than 0.05 | Less than 0.05 |
| (85) | 30 | Less than 0.05 | Less than 0.05 | Less than 0.05 | Less than 0.05 |
| (86) | 25 | Less than 0.05 | Less than 0.05 | Less than 0.05 | 0.1 |
| (87) | 15 | 0.1 | Less than 0.05 | Less than 0.05 | 0.1 |
| (88) | 14 | 0.1 | Less than 0.05 | 0.1 | 0.2 |

As shown in Table 13, only where the tablet is within a scope specified in the present invention, residual chlorine can be decreased in concentration to a very low level from immediately after start of dissolution of the tablet to complete dissolution thereof.

It has also been found that the effects of the present invention can be obtained preferably where the hardness is 15 kg or more, more preferably where it is 30 kg or more, and most preferably where it is 50 kg or more.

Example-11

In Experiment No. 1 of Reference Example-1, a load of 7 tons and a tablet making speed in Operation-3 were changed whenever necessary, loading time of a maximum load on making tablets was changed by the tablet making speed in particular, thereby producing tablets different in friability. And, pH was 7.0 when the tablet was dissolved in hot water at 40° C. The tablet hardness was set to be 50 kg.

TABLE 14

| Experiment No. (Tablet No.) | Friability (%) | ① When tablet was placed (ppm) | ② When tablet was consumed by 50% | ③ When tablet was consumed by 90% | ④ When tablet was completely dissolved |
|---|---|---|---|---|---|
| (89) | 0.5 | Less than 0.05 | Less than 0.05 | Less than 0.05 | Less than 0.05 |
| (90) | 10.2 | 0.1 | Less than 0.05 | Less than 0.05 | 0.2 |
| (91) | 10.0 | 0.1 | Less than 0.05 | Less than 0.05 | 0.1 |
| (92) | 5.0 | Less than 0.05 | Less than 0.05 | Less than 0.05 | 0.1 |
| (93) | 3.0 | Less than 0.05 | Less than 0.05 | Less than 0.05 | Less than 0.05 |

Table 14 has clearly shown that the friability is preferably 5.0 wt % or less in view of the effects of the present invention and more preferably 3.0 wt % or less.

Example-12

In Experiment No. 1 of Reference Example-1, a load of 7 tons in Operation-3 and a tablet making speed were changed whenever necessary, loading time of a maximum load on making tablets was changed by the tablet making speed in particular, thereby producing tablets different in friability. And, pH was 7.0 when the table was dissolved in hot water at 40° C. The tablet hardness was set to be 50 kg.

TABLE 15

| Experiment No. (Tablet No.) | Friability (wt %) | (B) Hair root mineral dirt | (C) Warmness of toes after washing | (D) Sound sleeping hours | (E) Fair skin (dullness-free and clear skin) |
|---|---|---|---|---|---|
| (94) | 0.5 | 5 | 5 | 5 | 5 |
| (95) | 10.2 | 4 | 3 | 3 | 3 |
| (96) | 10.0 | 5 | 4 | 3 | 4 |
| (97) | 5.0 | 5 | 5 | 4 | 5 |
| (98) | 3.0 | 5 | 5 | 5 | 5 |

It is apparent from Table 15 that where the friability is 10 wt % or less, the effects of the present invention are obtained and also apparent that from the results of (C) in particular, blood flow is improved to send blood sufficiently up to the peripheral capillary vessels, thereby warming the body. It is also apparent that where the friability is 5.0 wt % or less, the present invention exhibits more favorably the effects thereof, and it is apparent from the result of (C) in particular that blood flow in the peripheral blood vessels is further improved. Where the friability is 3.0 wt % or less, the present invention can exhibit the effects most favorably, and from the results of (D) in particular, the para-sympathetic nerve becomes predominant and blood flow is improved, thereby exhibiting the best results of sound sleeping hours.

What is claimed is:

1. A method for producing micro-bubbles mixed water, the method comprising:
   (a) guiding hot water through a water channel having a micro-bubble generating portion between an inlet port and an ejection port of the water channel, wherein in the micro-bubble generating portion the micro-bubbles are obtained by dissolving in the hot water a carbonated bathing agent accommodated in the micro-bubble generating portion, and (b) ejecting from the ejection port micro-bubbles mixed water, wherein the carbonated bathing agent is a compression molded tablet formed by compression molding in the presence of bicarbonate, an organic acid and polyethylene glycol, wherein the carbonated bathing agent is a tablet which is 7 mm or more both in a tablet diameter and a tablet thickness, 15 kg or more in tablet hardness, 10 wt % or less in tablet friability and from 5.5 to 9.0 in pH immediately after dissolution of the tablet in hot water, and wherein the carbonated bathing agent contains (i) at least one body rendering agent wherein the body rendering agent is alkane sulfonate with a carbon number of 6 to 18, olefin sulfonate with a carbon number of 6 to 18, sucrose fatty acid ester, sodium sulfate, or magnesium sulfate and (ii) at least one chlorine neutralizing compound wherein the chlorine neutralizing compound is L-ascorbic acid, L-ascorbate, thiosulfate, sulfite, erythobic acid, or erythobate.

2. The method according to claim 1, wherein the body rendering agent is contained at a ratio of 1:10 to 1:1000 in relation to the organic acid.

3. The method according to claim 1, wherein the chlorine neutralizing compound is contained at 8 wt % or less in relation to the organic acid.

4. The method according to claim 1, wherein the body rendering agent is the alkane sulfonate with a carbon number of 6 to 18 and the olefin sulfonate with a carbon number of 6 to 18.

5. A carbonated bathing agent for producing microbubbles mixed water by dissolving in hot water, the carbonated bathing agent comprising:

(a) a compression molded tablet formed by compression molding in the presence of bicarbonate, an organic acid and polyethylene glycol, wherein the tablet is 7 mm or more both in tablet diameter and tablet thickness, 15 kg or more in a tablet hardness, 10 wt % or less in tablet friability and from 5.5 to 9.0 in pH immediately after dissolution of the tablet in the hot water, and wherein the tablet contains (i) at least one body rendering agent wherein the body rendering agent is alkane sulfonate with a carbon number of 6 to 18, olefin sulfonate with a carbon number of 6 to 18, sucrose fatty acid ester, sodium sulfate, or magnesium sulfate and (ii) at least one chlorine neutralizing compound wherein the chlorine neutralizing compound is L-ascorbic acid, L-ascorbate, thiosulfate, sulfite, erythobic acid, or erythobate and wherein the chlorine neutralizing compound is contained at 8 wt % or less in relation to the organic acid.

6. The carbonated bathing agent according to claim 5, wherein the body rendering agent is contained at a ratio of 1:10 to 1:1000 in relation to the organic acid.

7. The carbonated bathing agent according to claim 5, wherein the body rendering agent is the alkane sulfonate with a carbon number of 6 to 18 and the olefin sulfonate with a carbon number of 6 to 18.

8. An apparatus for producing micro-bubbles mixed water; the apparatus comprising:

(a) a water channel at least partly defined by (i) a shower unit having a shower body portion and a shower head portion and (ii) a water supply hose;

(b) a micro-bubble generating portion fluidly exposed to the water channel; and (c) a carbonated bathing agent accommodated in the micro-bubble generating portion, the carbonated bathing agent comprising a compression molded tablet formed by compression molding in the presence of bicarbonate, an organic acid and polyethylene glycol, wherein the tablet is 7 mm or more both in tablet diameter and tablet thickness, 15 kg or more in a tablet hardness, 10 wt % or less in tablet friability and from 5.5 to 9.0 in pH immediately after dissolution of the tablet in the hot water, and wherein the tablet contains (i) at least one body rendering agent wherein the body rendering agent is alkane sulfonate with a carbon number of 6 to 18, olefin sulfonate with a carbon number of 6 to 18, sucrose fatty acid ester, sodium sulfate, or magnesium sulfate and (ii) at least one chlorine neutralizing compound wherein the chlorine neutralizing compound is L-ascorbic acid, L-ascorbate, thiosulfate, sulfite, erythobic acid, or erythobate.

9. The apparatus of claim 8, wherein the micro-bubble generating portion is located in the shower head portion.

10. The apparatus of claim 8, wherein the micro-bubble generating portion is located in the shower body portion.

11. The apparatus of claim 8, wherein the micro-bubble generating portion is located intermediate the shower body portion and the shower head portion.

12. The apparatus of claim 8, wherein the micro-bubble generating portion is located in a terminal end portion of the water supplying hose.

13. The apparatus of claim 8, wherein the micro-bubble generating portion is located in a leading end portion of the water supplying hose.

14. The apparatus of claim 8, wherein the micro-bubble generating portion is located intermediate a leading end portion of the water supplying hose and a terminal end portion of the water supplying hose.

15. The apparatus of claim 8, wherein the micro-bubble generating portion is detachably connected to the water channel.

16. The apparatus of claim 8, wherein the micro-bubble generating portion is detachably connected to the water channel by one-touch operation.

17. The apparatus of claim 8, wherein at least a portion of the micro-bubble generating portion is a transparent, so that at least one of a state of dissolution of the tablet accommodated in the micro-bubble generating portion and the presence or absence of the tablet can be visually observed.

18. The apparatus of claim 8, wherein at least a portion of the water channel is transparent and configured to provide visual observance of a water flow in the water channel.

* * * * *